(12) United States Patent
Young et al.

(10) Patent No.: US 9,463,286 B2
(45) Date of Patent: Oct. 11, 2016

(54) MEDICAMENT RESERVOIR FOR A MEDICATED MODULE

(75) Inventors: Alasdair George Young, Oxfordshire (GB); Daniel Thomas De Sausmarez Lintell, Warwickshire (GB)

(73) Assignee: SANOFI-AVENTIS DEUTSCHLAND GMBH, Frankfurt am Main (DE)

(*) Notice: Subject to any disclaimer, the term of this patent is extended or adjusted under 35 U.S.C. 154(b) by 343 days.

(21) Appl. No.: 14/110,546

(22) PCT Filed: Apr. 19, 2012

(86) PCT No.: PCT/EP2012/057160
§ 371 (c)(1),
(2), (4) Date: Oct. 8, 2013

(87) PCT Pub. No.: WO2012/143442
PCT Pub. Date: Oct. 26, 2012

(65) Prior Publication Data
US 2014/0031761 A1    Jan. 30, 2014

(30) Foreign Application Priority Data
Apr. 21, 2011 (EP) .................................. 11163404

(51) Int. Cl.
*A61M 5/32* (2006.01)
*B65B 3/00* (2006.01)
(Continued)

(52) U.S. Cl.
CPC ............ *A61M 5/3294* (2013.01); *A61M 5/326* (2013.01); *B65B 3/003* (2013.01); *A61J 1/201* (2015.05); *A61J 1/2013* (2015.05); *A61J 1/2093* (2013.01); *A61M 5/24* (2013.01); *A61M 5/2466* (2013.01); *A61M 5/3146* (2013.01);
(Continued)

(58) Field of Classification Search
CPC ...... A61M 5/19; A61M 5/3294; B65B 3/003
USPC .......... 141/255, 319, 329, 374; 604/411–415
See application file for complete search history.

(56) References Cited

U.S. PATENT DOCUMENTS 4,819,684 A    4/1989 Zaugg et al.
5,041,094 A *  8/1991 Perego .............. A61M 5/14526
                                              128/DIG. 12
(Continued)

FOREIGN PATENT DOCUMENTS

CH    445721     10/1967
DE    1909794    9/1970
(Continued)

OTHER PUBLICATIONS

International Preliminary Report on Patentability for Int. App. No. PCT/EP2012/057160, mailed Oct. 31, 2013.
(Continued)

*Primary Examiner* — Timothy L Maust
(74) *Attorney, Agent, or Firm* — McDonnell Boehnen Hulbert & Berghoff LLP

(57) ABSTRACT

A reservoir assembly for a medicated module includes a primary cavity for holding a medicament, a sump region, and a flexible element. The flexible element is configured to allow for fluid communication between the primary cavity and the sump region during a filling process for the reservoir. Further, the flexible element is configured to prevent fluid communication between the primary cavity and the sump region after the filling process.

11 Claims, 13 Drawing Sheets

(51) Int. Cl.
*A61M 5/24* (2006.01)
*A61M 5/31* (2006.01)
*A61M 5/315* (2006.01)
*A61M 5/178* (2006.01)
*B65B 31/00* (2006.01)
*A61J 1/20* (2006.01)

(52) U.S. Cl.
CPC ..... *A61M 5/31525* (2013.01); *A61M 5/31533* (2013.01); *A61M 5/3272* (2013.01); *A61M 2005/1787* (2013.01); *A61M 2005/3267* (2013.01); *B65B 31/00* (2013.01)

(56) References Cited

U.S. PATENT DOCUMENTS

| | | | | |
|---|---|---|---|---|
| 5,531,683 | A | * | 7/1996 | Kriesel ............... A61M 5/2429 604/416 |
| 5,971,953 | A | * | 10/1999 | Bachynsky ........... A61M 5/284 604/181 |
| 6,406,455 | B1 | * | 6/2002 | Willis .................... A61M 5/30 604/191 |
| 8,802,362 | B2 | * | 8/2014 | Grippi .............. A61B 17/00491 210/515 |
| 2004/0103951 | A1 | | 6/2004 | Osborne et al. |
| 2004/0199105 | A1 | | 10/2004 | Nussey |
| 2007/0175538 | A1 | | 8/2007 | Rothbauer et al. |

FOREIGN PATENT DOCUMENTS

| | | |
|---|---|---|
| DE | 2632334 | 1/1978 |
| JP | S62-243563 A | 10/1987 |
| JP | 2006-075356 A | 3/2006 |
| WO | 2010/139672 | 12/2010 |

OTHER PUBLICATIONS

International Search Report and Written Opinion for Int. App. No. PCT/EP2012/057160, mailed Sep. 5, 2012.

Japanese Office Action for JP Application No. 2014-505626, mailed Feb. 23, 2026.

* cited by examiner

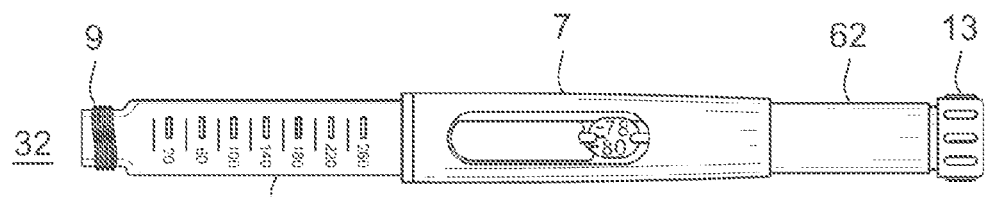
FIG. 1
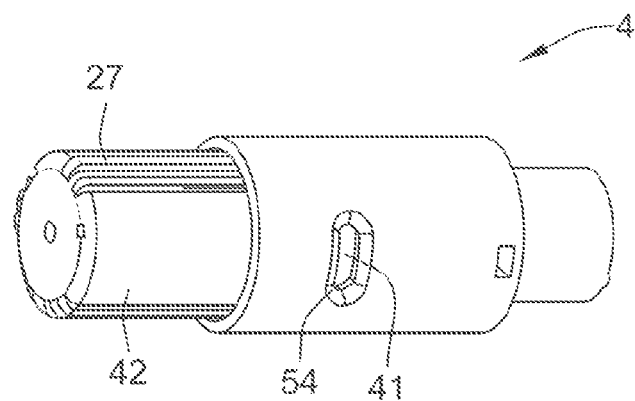
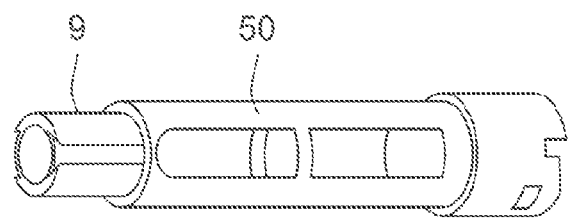
FIG. 2

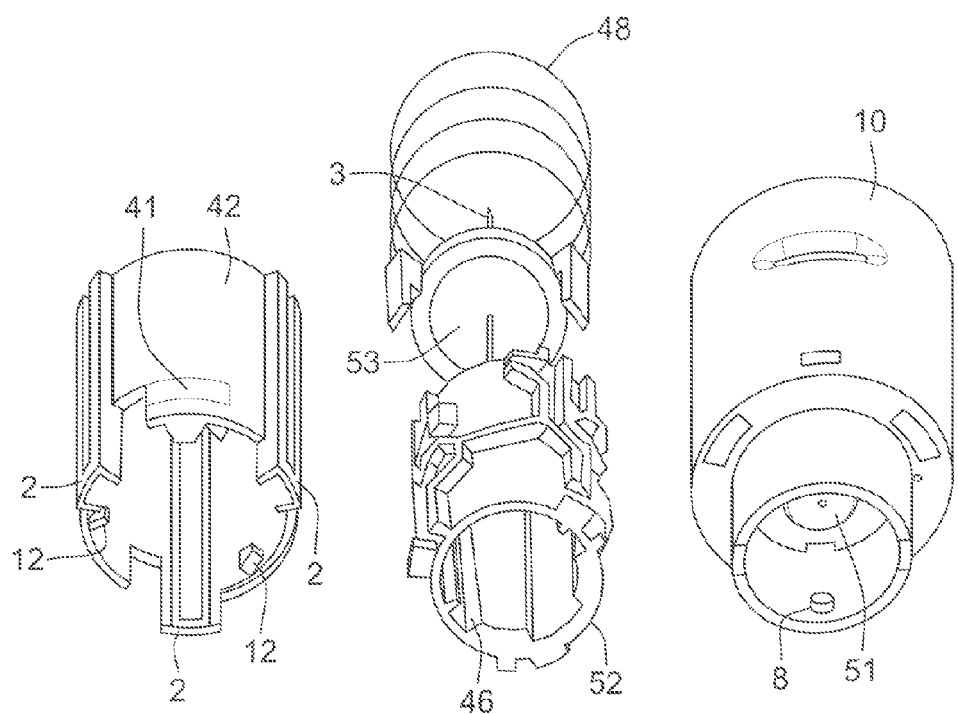
FIG. 4
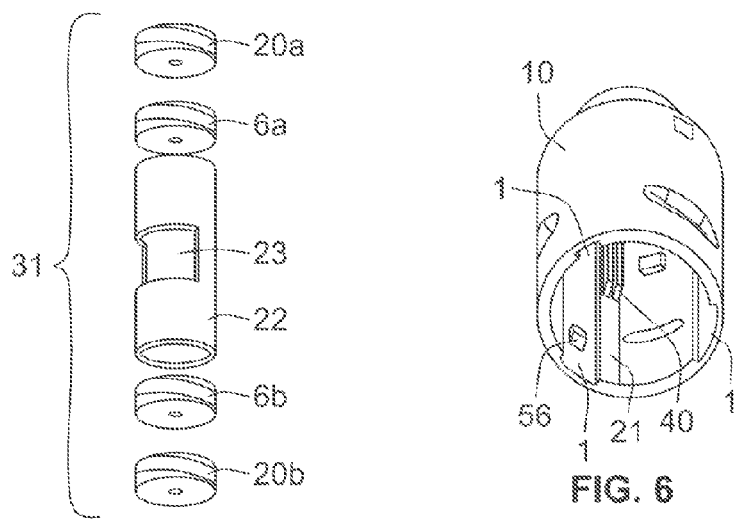
FIG. 5
FIG. 6

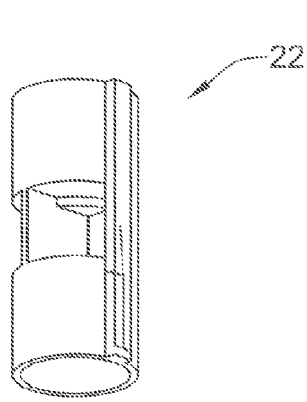
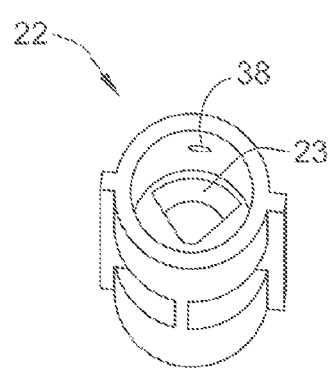
FIG. 9
FIG. 10
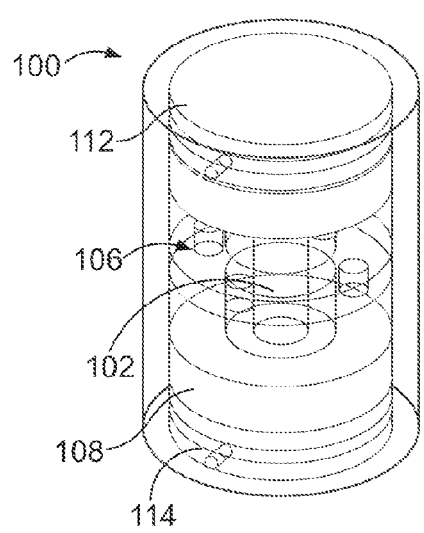
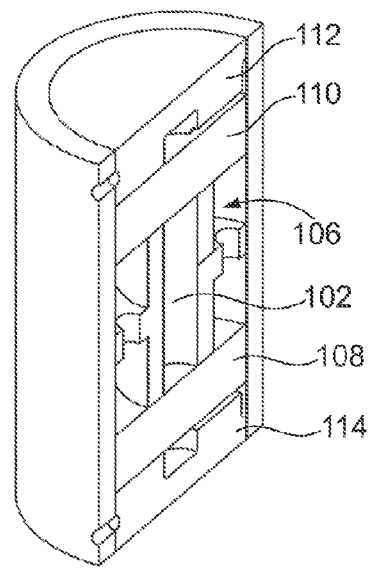
FIG. 11
FIG. 12a

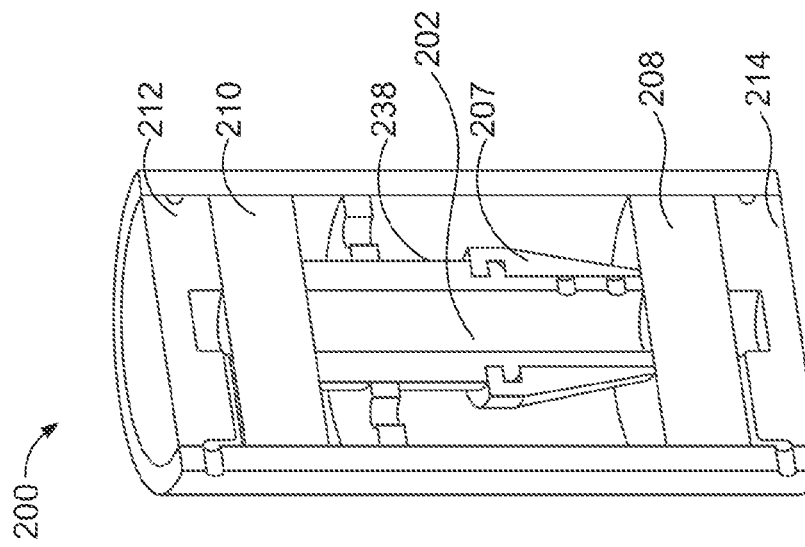
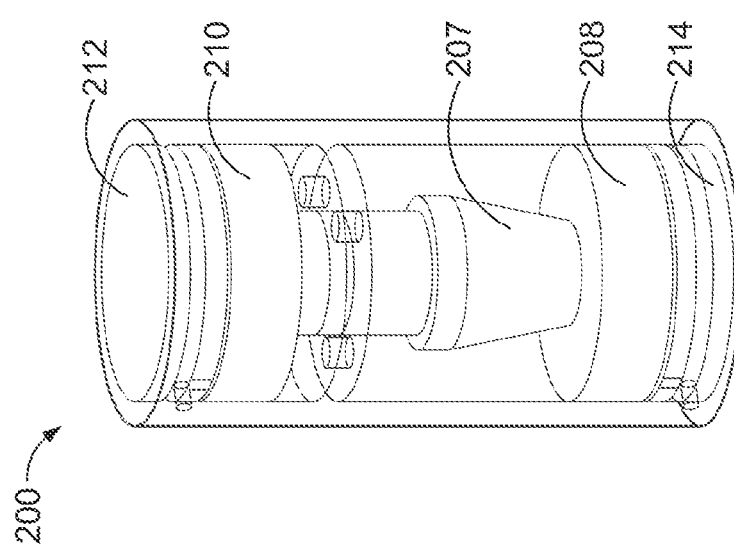

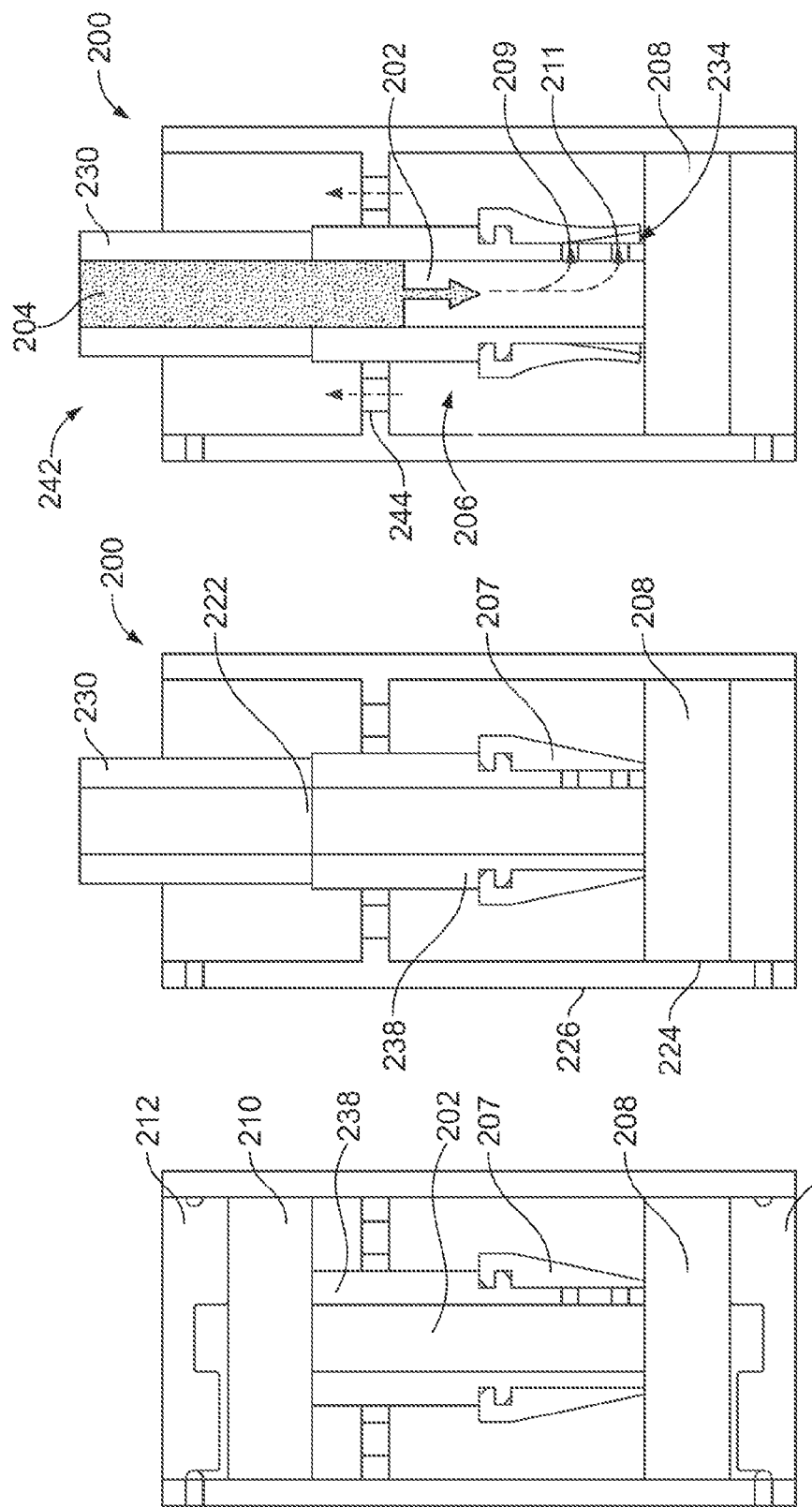

MEDICAMENT RESERVOIR FOR A MEDICATED MODULE

CROSS REFERENCE TO RELATED APPLICATIONS

The present application is a U.S. National Phase Application pursuant to 35 U.S.C. §371 of International Application No. PCT/EP2012/057160 filed Apr. 19, 2012, which claims priority to European Patent Application No. 11163404.4 filed Apr. 21, 2011. The entire disclosure contents of these applications are herewith incorporated by reference into the present application.

TECHNICAL FIELD

This disclosure relates to medical devices and delivering at least two drug agents from separate reservoirs using devices having only a single dose setting mechanism and a single dispense interface. A single delivery procedure initiated by the user causes a non-user settable dose of a second drug agent and a variable set dose of a first drug agent to be delivered to the patient. The drug agents may be available in two or more reservoirs, containers or packages, each containing independent (single drug compound) or pre-mixed (co-formulated multiple drug compounds) drug agents. A medicated module where the user does not have to manually select or set the module to dispense the second drug agent may be provided. Activation of the needle guard automatically causes the reservoir of secondary medicament to engage with dispensing conduits to allow a set dose of primary medicament and a single fixed dose of the of the secondary medicament to be injected. Specifically, the disclosure relates to a medicament reservoir for a medicated module that may be used with a drug delivery device.

BACKGROUND

Certain disease states require treatment using one or more different medicaments. Some drug compounds need to be delivered in a specific relationship with each other in order to deliver the optimum therapeutic dose. Applicants' proposed concept is of particular benefit where combination therapy is desirable, but not possible in a single formulation for reasons such as, but not limited to, stability, compromised therapeutic performance and toxicology.

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two medicaments or active agents simultaneously. The two active agents may interact with each other during the long-term, shelf life storage of the formulation. Therefore, it is advantageous to store the active components separately and only combine them at the point of delivery, e.g. injection, needle-less injection, pumps, or inhalation. However, the process for combining the two agents needs to be simple and convenient for the user to perform reliably, repeatedly and safely.

A further problem is that the quantities and/or proportions of each active agent making up the combination therapy may need to be varied for each user or at different stages of their therapy. For example one or more actives may require a titration period to gradually introduce a patient up to a "maintenance" dose. A further example would be if one active requires a non-adjustable fixed dose while the other is varied in response to a patient's symptoms or physical condition. This problem means that pre-mixed formulations of multiple active agents may not be suitable as these pre-mixed formulations would have a fixed ratio of the active components, which could not be varied by the healthcare professional or user.

Additional problems arise where a multi-drug compound therapy is required, because many users cannot cope with having to use more that one drug delivery system or make the necessary accurate calculation of the required dose combination. This is especially true for users with dexterity or computational difficulties. In some circumstances it is also necessary to perform a priming procedure of the device and/or needle cannulae before dispensing the medicaments. Likewise, in some situations, it may be necessary to bypass one drug compound and to dispense only a single medicament from a separate reservoir.

Accordingly, there exists a strong need to provide devices and methods for the delivery of two or more medicaments in a single injection or delivery step that is simple for the user to perform. Applicants' proposed concept overcomes the above-mentioned problems by providing separate storage containers for two or more active drug agents that are then only combined and/or delivered to the patient during a single delivery procedure. Setting a dose of one medicament automatically fixes or determines the dose of the second medicament (i.e. non-user settable). Applicants' proposed concept also gives the opportunity for varying the quantity of one or both medicaments. For example, one fluid quantity can be varied by changing the properties of the injection device (e.g. dialing a user variable dose or changing the device's "fixed" dose). The second fluid quantity can be changed by manufacturing a variety of secondary drug containing packages with each variant containing a different volume and/or concentration of the second active agent. The user or healthcare professional would then select the most appropriate secondary package or series or combination of series of different packages for a particular treatment regime.

Applicants' proposed concept also provides a medicated module that automatically causes the reservoir of secondary medicament to come into fluid communication with the primary medicament upon activation of the needle guard. This eliminates the need for the user to manually set or adjust the medicated module after performing a priming step.

Additionally, in some cases, accurate filling of a medicament reservoir for a medicated module may be difficult. For instance, accurate filling of the medicament and the incorporation of an amount of additional 'head-space' in the cavity in order to accommodate manufacturing and assembly tolerances may increase manufacturing costs. Further, it may be difficult to prevent air from entering the primary cavity of the reservoir. There is therefore also a need for a reservoir assembly configured to prevent air from entering the primary cavity of the reservoir.

These and other advantages will become evident from the following more detailed description of the invention.

SUMMARY

Applicants' proposed concept allows complex combinations of multiple drug compounds within a single drug delivery system. The proposed concept allows the user to set and dispense a multi-drug compound device though one single dose setting mechanism and a single dispense interface. This single dose setter controls the mechanism of the device such that a predefined combination of the individual drug compound is delivered when a single dose of one of the medicaments is set and dispensed through the single dispense interface.

By defining the therapeutic relationship between the individual drug compounds our delivery device would help ensure that a patient/user receives the optimum therapeutic combination dose from a multi-drug compound device without the inherent risks associated with multiple inputs where the user has to calculate and set the correct dose combination every time they use the device. The medicaments can be fluids, defined herein as liquids or powders that are capable of flowing and that change shape at a steady rate when acted upon by a force tending to change its shape. Alternatively, one of the medicaments may be a solid that is carried, solubilized or otherwise dispensed with another fluid medicament.

According to one specific aspect this proposed concept is of particular benefit to users with dexterity or computational difficulties as the single input and associated predefined therapeutic profile removes the need for them to calculate their prescribed dose every time they use the device and the single input allows considerably easier setting and dispensing of the combined compounds.

In a preferred embodiment a master or primary drug compound, such as insulin, contained within a multiple dose, user selectable device could be used with a single use, user replaceable, module that contains a single dose of a secondary medicament and the single dispense interface. When connected to the primary device the secondary compound is activated/delivered on dispense of the primary compound. Although our disclosure specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with Applicants' proposed concept.

For the purposes of this disclosure the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys(B3), Glu(B29) human insulin; Lys(B28), Pro (B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta¬ decanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH2).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

In one embodiment of Applicants' proposed concept there is provided a medicated module attachable to a drug delivery device that comprises an outer housing having a proximal end, a distal end, and an outer surface, where the proximal end preferably has a hub holding a double-ended needle and having a connector configured for attachment to a drug delivery device. There is a reservoir in a bypass housing within the outer housing that contains a medicament. The medicated module assembly of Applicants' proposed concept contains a needle guard that can reduce the risk of accidental needle sticks before and after use, reduce the anxiety of users suffering from needle phobia as well as preventing a user from using the device a subsequent time when the additional medicament has already been expelled.

The needle guard is preferably configured with a solid planar surface at its distal end that provides a large surface area that reduces the pressure exerted on the patient's skin, which allows the user to experience an apparent reduction in the force exerted against the skin. Preferably, the planar surface covers the entire distal end of the guard with the exception of a small needle pass through hole aligned axially with the needle. This pass through hole is preferably no more than 10 times greater in diameter than the outer diameter of the needle cannula. For example, with a needle outside diameter of 0.34 mm, the pass through hole diameter D can be 4 mm. Preferably, the pass through hole size should be large enough for the user to see that the device is primed (i.e., a drop or more of medicament) while not being so large that it is still possible to reach the end of the needle with a finger (i.e. needle stick injuries before or after use). This difference between the hole size and cannula diameter is to allow for tolerances, to allow users to see the drop of liquid on the end of the cannula after priming (whether a transparent or non-transparent guard is used) while keeping the size small enough to prevent accidental needle stick injuries.

Further, the movable needle guard or shield is configured to move axially in both the distal and proximal directions when pressed against and removed from an injection site. When the needle assembly is removed or withdrawn from the patient, the guard is returned to post-use extended position. A drive tooth on the inside surface of the guard engages a stop on a track on the outer surface of the bypass housing to securely lock the guard from further substantial axial movement. Preferably a lock out boss on the outer surface of the bypass housing is configured to engage a lock out feature on the inner proximal surface of the outer housing at the completion of the injection to further lock the medicated module from any further use and prevent the needle(s) and/or bypass component from being able to substantially move within the system even if the guard is held in an axially locked condition. By "substantial" movement we do not mean the typical amount of "play" in a system, but instead we mean that the guard and/or distal needle do not move axially a distance that exposes the distal end of the cannula once it is locked out.

One goal of Applicants' proposed concept is to eliminate the need to have the user manually operate the medicated module to change the state of the module from a priming state to a combination dose delivery state. Manually operated devices are sometimes not as intuitive as they could be and raise the risk of accidental misuse. Applicants' proposed concept solves this problem by utilizing energy stored within the module prior to delivery of the device to the user. The stored energy can come from a biasing member, such as a compressed spring. This stored energy is released during normal user operation of the module by actuating the mechanism and thus activating the state change from prime dose to combination dose. The mechanism aims to make this actuation imperceptible to the user, consequently making the user experience of the module very similar to that of a standard commercially available and accepted needle or safety needle (i.e. unpack module, attach to a drug delivery device, prime drug delivery device, inject a set dose along with single dose in the module). In this way, the module mechanism aims to reduce the risk of unintentional misuse and to improve usability by replicating an already accepted practice for similar injection methods.

As the module mechanism does not require the user to access external features on the module for the purposes of actuation, the number of components and subsequent module size can be reduced/optimized. These factors make the mechanism ideal for a single-use, high-volume manufacture, and disposable device application. Alternatively, as the actuation is driven by a single energy source, the system lends itself to a resettable actuation mechanism. The preferred embodiment described below is the single use (non-resettable) version. The lower hub is preferably restrained rotationally with regard to the needle guard, but is free to move axially within the needle guard. The needle guard is restrained rotationally with regard to the outer housing, but is free to move axially, between defined constraints, within the outer housing.

The user pressing the distal face of the needle guard against the skin causes axial motion of the needle guard in the proximal direction. This axial motion of the guard causes a rotation of the bypass housing through the engagement and action of an inward-facing drive tooth on the guard as it travels in a drive track having one or more paths, which is located on the outer surface of the bypass housing. After sufficient axial travel of the needle guard, the rotation of the bypass housing brings stand-offs inside the outer housing and at the proximal ends of the lower hub into line with pockets located on the outer surface of the bypass housing. Alignment of the stand-offs with the pockets allows the bypass housing to move axially in the proximal direction and further into the outer housing. The lower hub containing a double-ended needle cannula moves axially further onto the bypass housing. Both of these movements occur due to the relaxation/release of the stored energy of the biasing member, preferably a spring that is pre-compressed during module assembly or manufacture, and constitute "triggering" of the actuation mechanism. It is this axial movement of the lower hub onto the bypass housing and the corresponding movement of the bypass housing further into the outer body that results in the double ended needles located in the outer body distal end and the lower hub piercing the medicated module, moving it from a state of priming to combination dose delivery.

Further axial movement of the needle guard is required in order to pierce the skin, this retraction of the needle guard temporarily re-compresses the biasing member creating additional stored energy. At a "commit" point, the proximal axial movement of the drive tooth passes a non-return feature in the track through further rotation of the bypass housing. In normal use, once the drug has been dispensed and the needle is removed from the skin, the needle guard is allowed to return axially in the distal direction under the relaxation of the biasing member as it releases its stored energy. At some point along its return travel, the drive tooth contacts a further ramped face in one of the paths of the track, resulting in yet further rotation of the bypass housing. At this point, the outer housing stand-off comes into contact with a ramp feature on the outer surface of the bypass housing. The combination of this feature with the ramp between the drive tooth and the bypass housing track results in further biasing of the bypass housing stop face into the needle guard drive tooth. The stop face features act as an axial locking pocket. The action of the combined biasing force means that any axial load in the proximal direction put on the needle guard will result in the tooth being stopped in this pocket, locking out the needle guard from further use or exposing the needle. Should the user remove the device from the skin without dispensing fluid, but after the "commit" point has been passed, the needle guard would return to an extended position and lock out as previously described.

In one embodiment of Applicants' proposed concept there is provided a medicated module assembly attachable to a drug delivery device, preferably a pen shaped injection device, where the medicated module assembly comprises an outer housing having a proximal end and a distal end, where the proximal end has an upper hub holding a first double-ended needle cannula and a connector configured for attachment to a drug delivery device. The hub can be a separate part from the housing or integral, for example molded as part of the housing. The connector can be any connector design, such as threads, snap fits, bayonet, lure lock, or combination of these designs.

Two needle cannula are used, a distal cannula and a proximal cannula, with both cannulae preferably being doubled-ended for piercing a septum or seal and for piercing skin. The distal needle is mounted in a lower hub and the proximal needle is mounted in the upper hub, each using any technique known to those skilled in the art, such as welding, gluing, friction fit, over-molding and the like. The medicated module assembly also contains a biasing member, preferably a compression spring. The biasing member is preferably in a pre-compressed state and positioned between the proximal inner face of the needle guard and the distal face of the lower hub. Although a preferred biasing member is a spring, any type of member that produces a biasing force will work.

The medicated module assembly of Applicants' proposed concept automatically, once triggered, changes state from (1) a pre-use or priming state, where a small amount of primary medicament flows in a bypass around the reservoir containing a single dose of the secondary medicament, to (2) a ready-to-use or combination dose state, where both the upper and lower cannulae are in fluidic engagement with the fixed dose of the second medicament within the module and where a set dose of the primary medicament can be injected along with the non-settable single dose of secondary medicament in the reservoir, and finally to (3) a locked out state, where the needle guard is prevented from substantial proximal movement. The outer housing preferably has a window or indicator that shows the various states of the module. The indicator can be a pip, knob, button, or the like that protrudes through the outer surface of the proximal end of the needle guard and visually shows the user whether the module is in the pre-use or ready-to-use state. It may also be a visual indicator, e.g. showing colors or symbols, or a tactile or audible indicator. Preferably, user noticeable indicia indicate both a pre-use priming position and a locked position of the guard after the medicated module assembly has been used to perform an injection.

Inside the bypass housing there is a cavity that contains the capsule, which comprises the single dose of medicament in the reservoir. As the needle guard is retracted during an injection, the bypass housing is moved proximally along with the capsule positioned inside the cavity, thus decreasing the cavity volume. This allows the seals of the capsule to be pierced at its top and bottom by the needle cannula such that the medicament can be expelled from the reservoir during dose delivery. When connected to a drug delivery device containing a first medicament and prior to piercing the seals of the reservoir, the needle cannulae are only in fluid communication with the first medicament and a fluid flow path that bypasses the capsule. Preferably, a channel on the inside surface of the bypass housing is part of this fluid flow path and is used in the priming function of the drug delivery device.

As mentioned, the bypass housing preferably has one or more tracks located on the outside surface each having a set of first, second, third, and fourth paths. On the inner surface of the proximal end of the needle guard is one or more radial protrusions or drive teeth. As the guard first begins to refract, these protrusions travel in the first path causing the bypass housing to slightly rotate. As the guard continues to retract and then partially extend, the protrusions travel in the second and third paths. The protrusion moves to the fourth path and into a locking position when the guard is fully extended to its post-use position, which is preferably less extended than the starting position. The guard is rotationally constrained by the outer housing, preferably by the use of one or more spline features in the outer surface of the guard in cooperation with one or more followers or pips located at the distal end of the inner surface of the outer housing. The bypass housing is rotationally constrained when the protrusion is in the second path of the track. As the protrusion is moved axially in the proximal direction when the guard retracts, the protrusion moves from the second track to the third track causing the assembly to emit an audile sound and/or tactile feedback. This tells the user that the device will now be activated to lock upon extension of the guard in the distal direction.

A further aspect of Applicants' proposed concept relates to a method of dispensing a fixed dose of one medicament and a variable dose of a primary medicament from separate reservoirs that involves the steps of first attaching a medicated module to a delivery device set in a pre-use or prime only state. The user can prime the dose delivery device using only the primary medicament and bypassing the second medicament. After priming the user begins the injection and the needle guard begins to retract and the module automatically changes to second state that allows a combination delivery of the two medicaments. Upon completion of the delivery procedure and retraction of the needle from the injection site, the extension of the needle guard automatically changes the module to a third state.

During dispense, substantially the entire amount of second medicament has been expelled as well as the selected or dialed dose of the first medicament, through the single dispense interface. The capsule preferably contains a flow distributor to ensure that substantially all the single dose of secondary medicament is forced out of the capsule by the primary medicament during an injection. The flow distributor can be a separate stand alone insert or pin. Alternatively the flow distributor and the capsule together can be manufactured or assembled as a one-piece component where the flow distributor is integral with the capsule. Such a unitary construction can be achieved utilizing, for example, design principles such as form fit, force fit or material fit, such as welding, gluing, or the like, or any combination thereof. The one-piece component may comprise one or more medicament flow channels, preferably one flow channel. The capsule and/or flow distributor can be constructed of any material that is compatible to the primary and secondary medicaments. Preferably the capsule and/or flow distributor can be made from compatible materials of construction that include, but are not limited to, COC (an amorphous polymer based on ethylene and norbonene, also referred to as cyclic olefin copolymer, ethylene copolymer, cyclic olefin polymer, or ethylene-norbornene copolymer); LCP (a liquid crystal polymer having an aramid chemical structure that includes linearly substituted aromatic rings linked by amide groups, and further can include partially crystalline aromatic polyesters based on p-hydroxybenzoic acid and related monomers and also highly aromatic polyesters); PBT (polybutylene terephthalate thermoplastic crystalline polymer or polyester); COP (a cyclic olefin polymer based on ring-opening polymerization of norbornene or norbornene-derivatives); HDPE (high density polyethylene); and SMMA (styrene methyl methacrylate copolymer based on methyl methacrylate and styrene). A preferred material is one that is typically used to manufacture septa or pistons (bungs) found in multi-dose medicament cartridges, however, any other material that is compatible with the drug could be used, e.g., glass, plastics or specific polymers, for example, TPE (thermo plastic elastomer); LSR (liquid silicone rubber); LDPE (low density polyethylene); and/or any kind of medical grade rubber, natural or synthetic. By "substantially all" we mean that at least about 80% of the second medicament is expelled from the drug delivery device, preferably at least about 90% is expelled. In the third state, preferably the module is locked so as to prevent a second delivery or insertion by means of a locking mechanism as described previously.

The combination of compounds as discrete units or as a mixed unit is delivered to the body via an integral needle. This would provide a combination drug injection system that, from a user's perspective, would be achieved in a manner that very closely matches the currently available injection devices that use standard needles.

The medicated module of Applicants' proposed concept can be designed for use with any drug delivery device with an appropriate compatible interface. However, it may be preferable to design the module in such a way as to limit its use to one exclusive primary drug delivery device (or family of devices) through employment of dedicated/coded/exclusive features to prevent attachment of a non-appropriate medicated module to a non-matching device. In some situations it may be beneficial to ensure that the medicated module is exclusive to one drug delivery device while also permitting the attachment of a standard drug dispense interface to the device. This would allow the user to deliver a combined therapy when the module is attached, but would also allow delivery of the primary compound independently through a standard drug dispense interface in situations, such as, but not limited to, dose splitting or top-up of the primary compound.

A particular benefit of Applicants' proposed concept is that the medicated module makes it possible to tailor dose regimes when required, especially where a titration period is necessary for a particular drug. The medicated module could be supplied in a number of titration levels with obvious differentiation features such as, but not limited to, aesthetic design of features or graphics, numbering etc, so that a patient could be instructed to use the supplied medicated module in a specific order to facilitate titration. Alternatively, the prescribing physician may provide the patient with a number of "level one" titration medicated modules and then when these were finished, the physician could then prescribe the next level. A key advantage of this titration program is that the primary device remains constant throughout.

In an embodiment of Applicants' proposed concept, the primary drug delivery device is used more than once and therefore is multi-use; however, the drug delivery device may also be a single use disposable device. Such a device may or may not have a replaceable reservoir of the primary drug compound, but Applicants' proposed concept is equally applicable to both scenarios. It is also possible to have a suite of different medicated modules for various conditions that could be prescribed as one-off extra medication to patients already using a standard drug delivery device. Should the patient attempt to reuse a previously used medicated module, Applicants' proposed concept includes the locking needle guard that is activated after a first predefined travel/retraction of the guard/insertion of the needle. The locked needle guard would alert the patient to this situation and the inability to use the module for a second time. Visual warnings (e.g. change in color and/or warning text/indicia within an indication window on the module once insertion and/or fluid flow has occurred) can also be used. Additionally, tactile feedback (presence or absence of tactile features on the outer surface of the module hub following use) could be used as well.

A further feature of Applicants' proposed concept is that both medicaments are delivered via one injection needle and in one injection step. This offers a convenient benefit to the user in terms of reduced user steps compared to administering two separate injections. This convenience benefit may also result in improved compliance with the prescribed therapy, particularly for users who find injections unpleasant or who have computational or dexterity difficulties.

Applicants' proposed concept also covers a method of delivering two medicaments stored in separate primary packages. The medicaments may both be liquid, or alternatively one or more of the medicaments may be a powder, suspension or slurry. In one embodiment the medicated module could be filled with a powdered medicament that is either dissolved or entrained in the primary medicament as it is injected through the medicated module.

In accordance with a further embodiment of Applicants' disclosure, a reservoir assembly for a medicament module is provided. The reservoir assembly is configured to minimize or eliminate the presence of air in the primary drug cavity in a reservoir assembly for a medicated module. Similarly, a method may be provided that minimizes or eliminates the presence of air in the primary drug cavity in a reservoir assembly for a medicated module.

One aspect of the invention relates to a reservoir assembly that beneficially results in little or no air being present in the reservoir cavity after filling. The reservoir assembly in accordance with Applicants' proposed concept generally incorporates two elements: a sump region and the medicament cavity. An example purpose of the sump region is to increase the nominal fill volume relative to the primary cavity volume. This increase may reduce the challenges associated with filling the device due to the possible small volume (e.g., 20-30 microliters (µl)) required by the drug cavity. Other volumes are possible as well, such as higher or lower volumes. In addition, the interface between the sump region and the primary cavity is configured such that during filling air is preferably purged from the drug cavity into the sump region. This air-purging action serves to help minimize any residual air trapped in the medicament cavity and thus minimizes its impact on the dispense volume when the cavity contents are expelled during use. The primary cavity is designed and sized to suit the required volume for the medicated module such that a known and controlled volume of the second medicament will be dispensed when the minimum required dose (e.g., in the range 50 µl) is dispensed from the primary drug delivery device to which the medicated module is attached.

In accordance with the invention of Applicants' disclosure, a reservoir assembly for a medicated module includes a primary cavity for holding a medicament, a sump region, and a flexible element. The flexible element is configured to allow for fluid communication between the primary cavity and the sump region during a pressure filling process for the reservoir. Further, the flexible element is configured to prevent fluid communication between the primary cavity and the sump region after the filling process. In an example, the flexible element may be a flexible bung. In another example, the flexible element may be a flexible vent valve.

Generally, during a filling process or pressure filling process for the reservoir assembly, the medicament from a pressurized filling nozzle will cause a flexible element (e.g., a flexible lower bung) in the reservoir assembly to deflect and thus to create a vent path to the sump region. This vent path will enable air to be purged/forced from the drug cavity and into the sump region. After filling, the pressure may be removed and the flexible element will return to its former position, sealing off the drug cavity from the sump region. The upper bung is then assembled to create the sealed drug cavity. Preferably the stiffness of the flexible element (which may be defined by a combination of material properties and geometry) will be designed such that the hydraulic pressure generated during an in-use dispense action will be insufficient to cause sufficient deflection to re-open this flow path between the drug cavity and the sump region again.

The flexible element may be arranged between the primary reservoir and the sump region. Alternatively, the flexible element may be arranged to separate the primary reservoir and the sump region.

The flexible element may be part of a fluid connection or an interface between the primary cavity and the sump region in order to enable fluid communication. In one example, at least a portion of the flexible element may be at an interface between the primary cavity and the sump region.

The sump region may be configured to collect excess air and/or medicament from the primary cavity during a filling process of the reservoir assembly.

The primary cavity may comprise a tubular cavity. The tube may be closed by bungs on both ends. The tube may be closed by a bung on one end during filling. The tube may be closed by bungs on both ends after filling.

During filling, medicament may be driven into the primary cavity under pressure. The filling action may cause the flexible element to allow for fluid communication between the primary cavity and the sump region. After filling, the pressure may be removed which causes the flexible element to prevent fluid communication between the primary cavity and the sump region.

In accordance with Applicants' disclosure, a reservoir assembly for a medicated module includes a primary cavity for holding a medicament, a sump region, and a flexible element. The primary cavity may be located along a central axis of the medicated module. The sump region may be arranged radially outward with regards to the primary cavity. The sump region may comprise one or more cavities arranged radially outward with respect to the primary cavity. The sump region may comprise one or more cavities arranged around a central primary cavity. In one embodiment, the sump region comprises two or more cavities arranged around a central primary cavity. In another embodiment, the primary cavity may be a tubular cavity, and the sump region may be a ring-shaped tubular cavity surrounding the primary cavity.

A method for filling a reservoir assembly is also provided. The method includes providing a reservoir assembly comprising (i) a primary cavity, (ii) a sump region, and (iii) a flexible element, wherein at least a portion of the flexible element is at an interface between the primary cavity and the sump region. Further, the method includes a filling nozzle forming a seal against an upper surface of the primary cavity. Still further, the method includes the filling nozzle forcing air from the primary cavity to the sump region, wherein forcing the air from the primary cavity to the sump region comprises forcing the flexible element to deflect, thereby opening up a flow path from the primary cavity to the sump region. And yet still further, the method includes the filling nozzle filling the primary cavity with medicament and the filling nozzle at least partially filling the sump region with the medicament.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 1 illustrates one possible drug delivery device that can be used with Applicants' proposed concept;

FIG. 2 illustrates an embodiment of the medicated module of Applicants' proposed concept, where the medicated module is separated from an attachable cartridge holder of drug delivery device;

FIG. 4 illustrates an exploded proximal perspective view of all the components (except the medicated capsule) of the medicated module illustrated in FIG. 2;

FIG. 5 is a perspective view of the capsule containing the reservoir of the embodiment of FIG. 2;

FIG. 6 illustrates a proximal perspective view of the outer housing of the embodiment of FIG. 2;

FIG. 9 illustrates an example reservoir for a medicated module;

FIG. 10 illustrates and example flow distributor for a medicated module;

FIG. 11 illustrates a perspective view of an example reservoir assembly in accordance with an embodiment of Applicants' disclosure;

FIG. 12a illustrates a perspective cross-sectional view of the reservoir assembly of FIG. 11;

FIG. 15 illustrates a perspective view of another example reservoir assembly in accordance with an embodiment of Applicants' disclosure;

FIG. 16a illustrates a perspective cross-sectional view of the reservoir assembly of FIG. 11;

FIG. 16b illustrates a cross-sectional view of the reservoir assembly of FIG. 11;

FIGS. 17a-f illustrate the reservoir assembly of FIG. 11 at various stages of the assembly and filling process.

DETAILED DESCRIPTION

Figure 3:
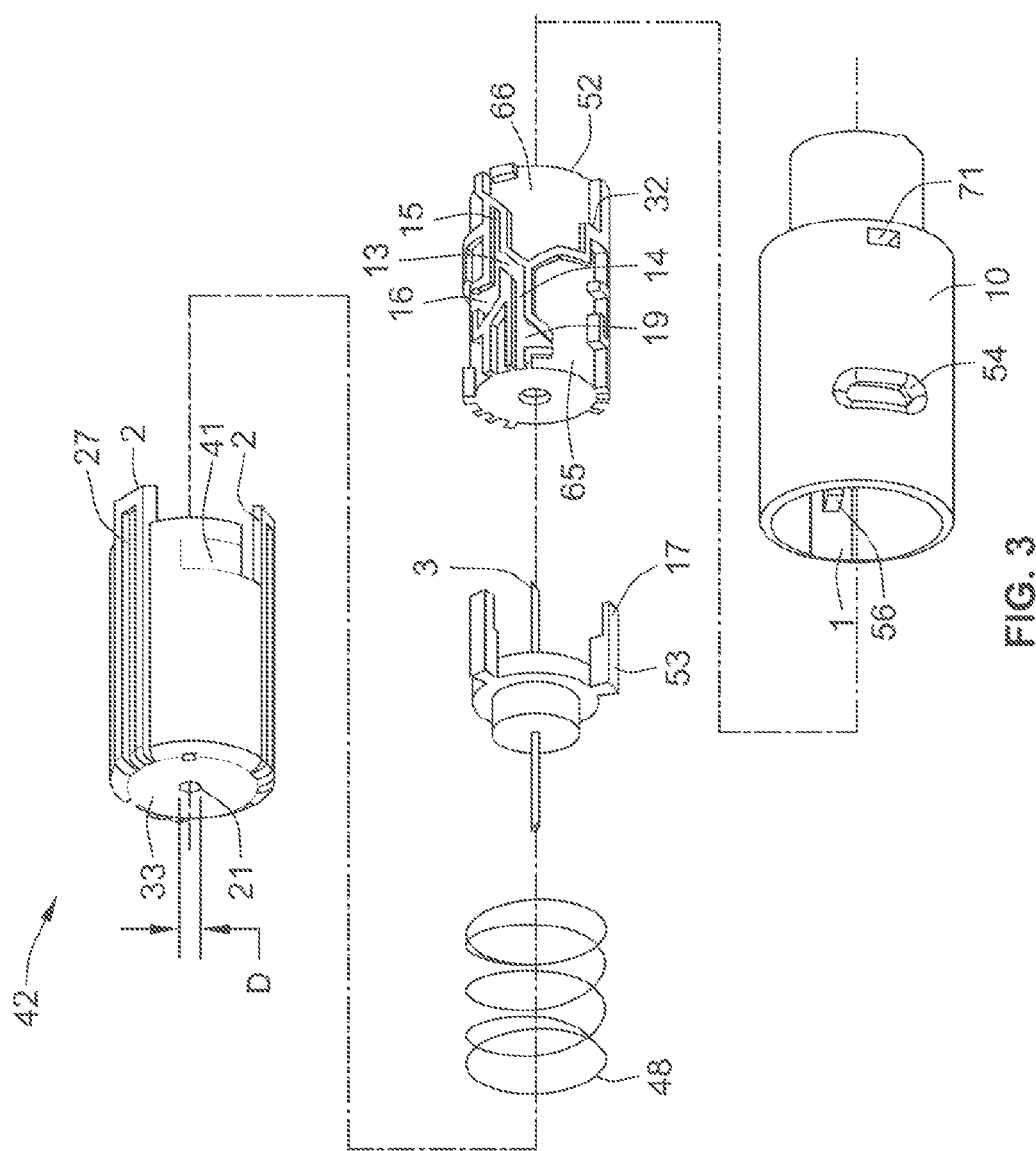
FIG. 3 illustrates an exploded distal perspective view of all the components (except the medicated capsule) of the medicated module illustrated in FIG. 2.

Applicants' proposed concept administers a fixed predetermined dose of a secondary drug compound (medicament) and a variable dose of a primary or first drug compound through a single output or drug dispense interface. Setting the dose of the primary medicament by the user automatically determines the fixed dose of the second medicament, which preferably is a single dose contained in a capsule or reservoir having an integral flow distributor. In a preferred embodiment the drug dispense interface is a needle cannula (hollow needle). FIG. 1 illustrates one example of a drug delivery device 7 that the medicated module 4 (see FIG. 2 or 7) of Applicants' proposed concept can be attached to the connection means 9 on cartridge holder 50 of distal end 32. Each medicated module is preferably self-contained and provided as a sealed and sterile disposable module that has an attachment means 8 compatible to the attachment means 9 at the distal end 32 of device 7. Although not shown, the medicated module could be supplied by a manufacturer in a protective and sterile container, where the user would peel or rip open a seal or the container itself to gain access to the sterile medicated module. In some instances it might be desirable to provide two or more seals for each end of the medicated module.

Figure 7:
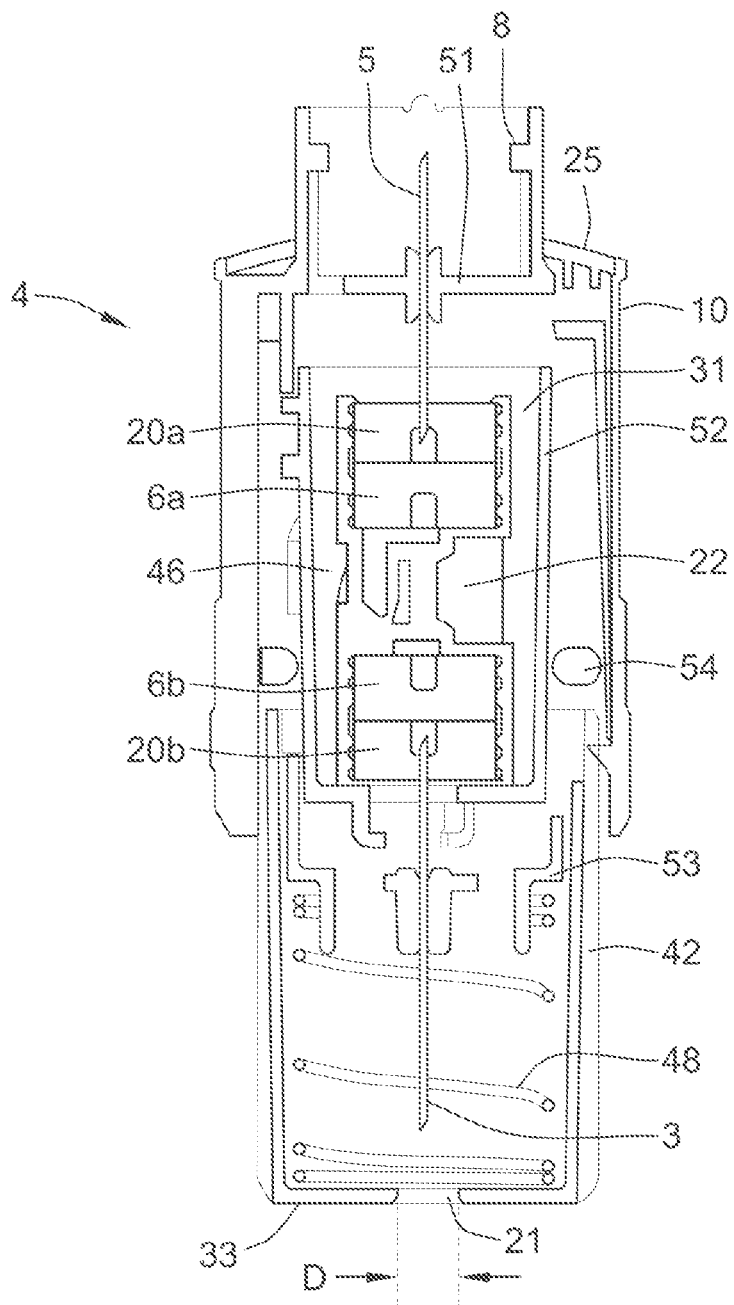
FIG. 7 is a sectioned view of the embodiment of the medicated module shown in FIG. 2 orientated in the bypass configuration.

Any known attachment means 8 can be used to attach the medicated module to the chosen drug delivery device, including all types of permanent and removable connection means, such as threads, snap locks, snap fits, luer locks, bayonet, snap rings, keyed slots, and combinations of such connections. FIGS. 2, 4, and 7 illustrate the attachment means 9 as a unique bayonet type connection that is keyed specifically to a corresponding female bayonet type connection 8 on hub 51 of medicated module 4. The embodiments shown in FIGS. 2, 4, 5, and 7 have the benefit of the second medicament as a single dose being contained entirely within capsule 31, and specifically in reservoir 22, hence minimizing the risk of material incompatibility between the second medicament and the materials used in the construction of the medicated module 4, specifically housing 10, bypass housing 52, or any of the other parts used in the construction of the medicated module.

To minimize the residual volume of the second medicament, caused by recirculation and/or stagnant zones, that might remain in capsule 31 at the end of the dispense operation, it is preferable to have a flow distributor 23 as an integral part of reservoir 22 (see FIG. 5). The reservoir 22 containing the single dose of the secondary medicament can be sealed with septa 6a and 6b (also referred to below as "primary-cavity bungs"), which are fixed to the capsule using keepers or plugs 20a and 20b (also referred to below as "bypass bungs"). Preferably the keepers have fluid channels that are in fluid communication with needles 3 and 5 and with bypass 46, which is preferably part of the inside surface of bypass housing 52. Together this fluid path allows priming of the drug delivery device before injection. Preferably the reservoir, flow distributor, keepers, and bypass can be made from materials that are compatible with the primary medicament. Examples of compatible materials of construction include, but are not limited to, COC (an amorphous polymer based on ethylene and norbornene, also referred to as cyclic olefin copolymer, ethylene copolymer, cyclic olefin polymer, or ethylene-norbornene copolymer); LCP (a liquid crystal polymer having an aramid chemical structure that includes linearly substituted aromatic rings linked by amide groups, and further can include partially crystalline aromatic polyesters based on p-hydroxybenzoic acid and related monomers and also highly aromatic polyesters); PBT (polybutylene terephthalate thermoplastic crystalline polymer or polyester); COP (a cyclic olefin polymer based on ring-opening polymerization of norbornene or norbornene-derivatives); HDPE (high density polyethylene); and SMMA (styrene methyl methacrylate copolymer based on methyl methacrylate and styrene). The needle pierceable septa, bungs, and/or seals that are used with both the capsule and the primary medicament cartridge can be manufactured using TPE (thermo plastic elastomer); LSR (liquid silicone rubber); LDPE (low density polyethylene); and/or any kind of medical grade rubber, natural or synthetic.

The design of flow distributor 23 should ensure that at least about 80% of the second medicament is expelled from reservoir 22 through the distal end of needle 3. Most preferably at least about 90% should be expelled. Ideally, displacement of the first medicament in a primary reservoir (not shown) contained in cartridge holder 50 and through the capsule 31 will displace the single dose of the second medicament stored in reservoir 22 without substantial mixing of the two medicaments.

Attachment of the medicated module 4 to the multi-use device 7 causes proximal needle 5 to penetrate a septum (not shown) sealing the distal end of the cartridge of primary medicament positioned in cartridge holder 50 of the multi-use device 7. Once needle 5 has passed through the septum of the cartridge, fluid connection is made between the first medicament and the needle 5. At this point, the system can be primed by dialing out a small number of units (or cocking the device if only a single dose selection is possible) using dose dial sleeve 62. Once the device 7 is primed, activation of the needle guard 42 allows dispense of the medicaments by subcutaneously injecting the medicaments via activation of a dose button 13 on device 7. The dose button of Applicants' proposed concept can be any triggering mechanism that causes the dose of the first medicament that was set by the dose dial sleeve 62 to move towards the distal end 32 of the device. In a preferred embodiment the dose button is operably connected to a spindle that engages a piston in the primary reservoir of the first medicament. In a further embodiment the spindle is a rotatable piston rod comprising two distinct threads.

One embodiment of the medicated module 4 of Applicants' proposed concept is illustrated in FIGS. 2 and 7. In these embodiments the medicated module 4 contains a capsule 31 comprising a reservoir 22, two keepers 20a and 20b, and two seals 6a and 6b. Reservoir 22 contains a fixed single dose of a secondary medicament. In some cases this secondary medicament may be a mixture of two or more drug agents that can be the same or different from the primary drug compound in the drug delivery device 7. Preferably the capsule is permanently fixed within the medicated module, however, in some cases it may be preferred to design the module such that the capsule can be removed when empty and replaced with a new capsule.

In the embodiments shown in FIGS. 5 and 7, capsule 31 has ends that are sealed with pierceable membranes or septa 6a and 6b that provide a hermetically sealed and sterile reservoir 22 for the second medicament. A primary or proximal engagement needle 5 can be fixed in hub 51 connected to the proximal end of housing 10 of the module and configured to engage capsule 31 when needle guard is moving in the proximal direction during injection. The outlet, or distal needle 3, is preferably mounted in lower hub 53 and initially protrudes into lower keeper 20b. The proximal end of needle 3 pierces the lower septum 6b when the bypass housing 52 rotates and is moved proximally by the force exerted by needle guard 42 and spring 48 during injection.

When first attached to the delivery device, the medicated module 4 is set at a pre-use or starting position. Preferably, indicator 41 shows through window 54 to inform the user of the pre-use condition of the medicated module. The indicator is preferably a color stripe or band on the outer surface of the proximal end of guard 42 (see FIG. 3) visible through an aperture in the outer body. The needle guard 42 is slidably engaged with inner surface of outer housing 10 by engagement of arms 2 and channels 1. Retention snaps 56 prevent the guard from disengaging the outer housing at its fully extended position. Housing 10 partially defines an internal cavity 21 that holds bypass housing 52, which contains capsule 31. A portion of the proximal end of housing 10 defines an upper hub 51 that holds needle 5. Optionally, as illustrated in FIG. 7, a shoulder cap 25 may be added to the proximal outer surface of outer housing 10. This shoulder cap can be configured to serve as indicia to identify to a user the type/strength of medicament contained in the module. The indicia can be tactile, textual, color, taste or smell.

FIG. 7 shows a cutaway or cross-sectioned view of the medicated module set in a pre-use or starting state where needles 3 and 5 are not piercing septa 6a and 6b. In this position, the bypass housing 52 is at its most extended position and needles 3 and 5 are not in fluid communication with medicament contained in capsule 31. The capsule is supported by bypass housing 52. In this neutral or suspended state of capsule 31, primary medicament from the cartridge in cartridge holder 50 of device 7 can flow through needle 5 into keeper 20a, through bypass 46 and into keeper 20b, and eventually out through needle 3. This flow configuration allows a user to perform a priming step or procedure by setting a small dose of the primary medicament using the dose dial sleeve 62 and dose button 13 on the drug delivery device 7.

The compression spring 48 is positioned between the distal end of the lower hub 53 and the inner proximal face of guard 42 to bias the guard 42 into an extended (guarded) position as illustrated in FIG. 7. Upon assembly, spring 48 is purposely compressed to supply a proximally directed biasing force against lower hub 53. This pre-compression of spring 48 is possible because the lower hub 53 and the bypass housing 52 are prevented from moving in an axial proximal direction by radial stand off 40 located on the inside surface of the outer housing (FIG. 6) that engage with an upper stand off pocket 66 and legs 17 of lower hub 53 engaging lower stand off pocket 65. The combination of these stand-offs/legs and pockets prevent the lower hub and upper hub needles from piercing into the centre of the capsule until the device is triggered as previously described.

The proximal inside surface of guard 42 has one or more inwardly protruding features, drive teeth, pips, or like structures 12 that run in one or more tracks 13 or guide ways formed in the outer surface of bypass housing 52. As shown in FIG. 3, track 13 can be described as four paths, 19, 14, 15, and 16, that have a specific geometry such that after a single use of the medicated module 4 the drive tooth 12 is blocked from further axial movement and the guard (and device) is "locked" in a guarded position where the distal end of the needle is completely and safely covered by guard 42.

One unique feature of our medicated module assembly is the user feedback that is given when the assembly is used. In particular, the assembly could emit an audible and/or tactile "click" to indicate to the user that they have firstly triggered the device and secondly reached the "commit" point such that the needle guard will lock safely out upon completion of the injection/removal of the guard from the injection site. This audible and/or tactile feature could work as follows. As mentioned, the needle guard 42 is rotationally constrained by outer housing 10 and has one or more drive teeth 12 that are initially in path 19 of track 13 on bypass housing 52. As the guard is moved proximally, the spring 48 is further compressed exerting additional force in the proximal direction on lower hub 53, which is initially constrained axially by the lower stand off pocket 65 engaged with legs 17. Likewise, the bypass housing 52 is constrained from moving proximally by upper stand off pocket stop 32 engaged with stand off 40 on the inner surface of outer housing 10. The drive teeth 12 travel in path 19 causing the bypass housing to rotate slightly. This rotation will disengage the upper stand off 40 from upper standoff pocket stop 32, allows the drive teeth to enter path 14, and unblocks legs 17 from lower standoff pocket allowing the bypass housing to move proximally carrying with it capsule 31, where it then can engage needles 3 and 5. As the guard continues to move proximally, the drive teeth move from path 14 passed transition point 14a into path 15 causing further rotation of the bypass housing. As this rotation is completed the drive teeth transition to path 13, potentially emitting an audile "click" sound, as well as a tactile feel, to the user. This transition past point 15a (and the corresponding point directly below it on the track) constitute the "commit" point and as such, once it has been reached the needle guard 42 will "lock out" when it extends upon removal of the device from the injection site.

As mentioned, the distal end of the guard 42 has a planar surface 33 that provides an added measure of safety and reduces the pressure exerted by the guard on the injection site during an injection with our needle assembly. Because the planar surface 33 substantially covers access to needle 3 a user is prevented from gaining access to the distal tip of the needle after the assembly is in the locked position. Preferably, the diameter D of needle pass through hole 21 in the planar surface is no more than 10 times that of the outer diameter of needle cannula 3.

The outer proximal surface of the needle guard 42 preferably has indicia 41 that are preferably at least two different color stripes or bands, each of which is sequentially visible through the opening or window 54 in outer housing 10. One color could designate the pre-use or prime state of the module and the other color would indicate that the module is in finished or locked state, another color could be used to denote the transition through the trigger or "commit" point in case a user stops injection after trigger point but before "commit" point. For example, a green color could be the pre-use position and a band of red color could be used to indicate that the module has been used and is locked and an orange color could indicate that the device has been triggered but not locked out. Alternatively, graphics, symbols or text could be used in place of color to provide this visual information/feedback. Alternatively these colors could be displayed using the rotation of the bypass cavity and printed on or embedded into the bypass housing. They could be visible through the aperture by ensuring that he needle guard is made form a transparent material.

Figure 8:
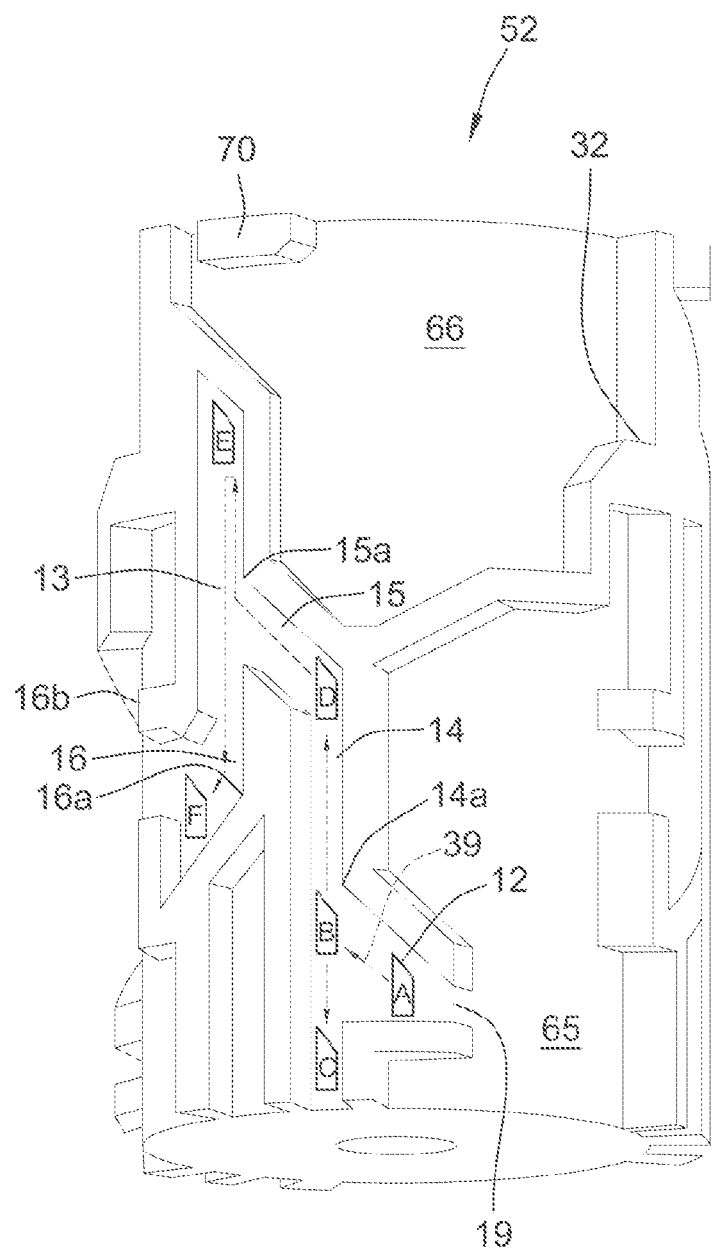
FIG. 8 is a close-up perspective view of the bypass housing of the embodiment of the medicated module shown in FIG. 2 to illustrate the positions of the drive tooth during use.

FIG. 8 illustrates the travel of drive teeth 12 in one or more tracks 13 as illustrated by directional arrow 39. Drive tooth 12 begins at position A and through axial movement of the needle guard biases the bypass housing rotationally until it moves past the transition point 14a and arrives at position B. Once the drive tooth reaches position B the bypass housing and lower needle hub move proximally causing the capsule 31 to engage needles 3 and 5, and the drive tooth moves relatively to position C (this is termed as the triggering of the device) and it is the bypass housing/lower hub moving proximally under the release of stored energy that results in the effective position of the needle guard drive tooth being position C. It is important to note that the needle guard does not move under the action of the release stored energy, it is just the needle hub and the bypass housing that move relatively away from the needle guard at the point of triggering, hence the drive tooth moves from position B to position C. As the needle guard continues to retract, drive tooth 12 moves proximally in path 14 to position D, where it exerts a rotational bias on the bypass housing 52 causing it to rotate again until tooth 12 passes the transition 15a (commit point) into path 13. The drive tooth then moves proximally until position E is reached. At this point, the needle guard 42 is fully retracted and the full available insertable length of the needle is exposed. Once the user removes the guard from contact with the skin, the guard begins to extend as a result of the distal biasing force exerted by spring 48 on the inner proximal surface of the guard. The utilization of the stored energy spring to act both as a trigger/piercing spring and also, once extended post triggering, as the needle guard spring is a unique aspect of this design. It negates the need to use two separate springs for these separate functions by locating the spring in a position such that it can fulfill both roles. Initially, for example during assembly or manufacture of the medicated module, the biasing member is compressed exerting a force on the lower hub/bypass housing in preparation for triggering. Once triggered it extends proximally where upon it can then be compressed from the distal end as the needle guard retracts against it. This secondary compression provides the force to push the needle guard back to the extended and locked position as it is removed from the injection site. As the guard moves to its fully extended post-use position, which preferably is less extended than the starting position, the drive tooth 12 moves distally in path 13 until it reaches transition point 16a, where it then rotationally biases the bypass housing 52 to rotate yet again until tooth 12 enters path 16 and arrives at position F. This last rotation of bypass housing 52 causes lock out boss 70 to engage lock out feature 71. This prevents any further rotational or axial movement of the bypass housing. The needle guard is prevented from further substantial axial movement, as defined earlier, by engagement of the drive tooth with axial stop 16b. It is within the scope of Applicants' proposed concept that a number of tooth arrangements and/or profiles could be used to fulfill the required function described above, e.g., simple equal tooth profiles or more complex multi-angled profiles. The particular profile being dependent upon the required point of commit and rotation of the bypass housing. It is also within the scope of Applicants' proposed concept that a similar axial/rotational locking of the lower needle hub to the bypass housing as of the bypass housing to the outer housing, could be integrated to prevent movement of the needle post-triggering and post-lock out.

In any of the above described embodiments of Applicants' proposed concept the second medicament may be either in a powdered solid state, any fluid state contained within the secondary reservoir or capsule, or coated to the inside surface of the drug dispense interface. The greater concentration of the solid form of the medicament has the benefit of occupying a smaller volume than the liquid having lower concentration. This in turn reduces the ullage of the medicated module. An additional benefit is that the solid form of the second medicament is potentially more straightforward to seal in the secondary reservoir than a liquid form of the medicament. The device would be used in the same manner as the preferred embodiment with the second medicament being dissolved by the first medicament during dispense.

To minimize diffusion of the secondary medicament contained in the capsule within the medicated module into the primary medicament during dispense of the medicaments the reservoir 22 has an integral flow distributor 23. This flow distributor also ensures efficient expulsion of the second medicament from the system and minimizes residual volume. One possible embodiment of the reservoir 22 and flow distributor 23 is illustrated in FIGS. 9 and 10. Preferably the reservoir and flow distributor are manufactured as a single part from materials that are compatible with the secondary medicament, most preferably as a single molded piece. A preferred material would be that typically used to manufacture septa or pistons (bungs) found in multi-dose medicament cartridges, although any material that is compatible with the medicament during long term storage would be equally applicable. The flow distributor 23 is configured and positioned in reservoir 22 such that the secondary medicament fills flow channels that are defined by the shape and location of one or more channels (not shown) inside the reservoir. The shape of the flow channels can be optimized for a plug flow of medicament by varying the dimensions of the flow distributor and/or channels. The cross-sectional area of the annulus formed between the flow distributor and the wall of the reservoir should be kept relatively small. The volume available to store the secondary medicament would equal the internal volume of the reservoir minus the volume of the flow distributor. Therefore if the volume of the flow distributor is marginally smaller than the internal volume of the capsule, a small volume is left which the secondary medicament occupies. Hence the scale of both the capsule and the flow distributor can be large while storing a small volume of medicament. Resultantly for small volumes of secondary medicament (e.g. 50 micro liters) the reservoir can be of an acceptable size for handling, transport, manufacture, filling and assembly.

Preferably the medicated module is provided by a drug manufacturer as a stand-alone and separate device that is sealed to preserve sterility. The sterile seal of the module is preferably designed to be opened automatically, e.g. by cutting, tearing or peeling, when the medicated module is advanced or attached to the drug delivery device by the user. Features such as angled surfaces on the end of the injection device or features inside the module may assist this opening of the seal.

The medicated module of Applicants' proposed concept should be designed to operate in conjunction with a multiple use injection device, preferably a pen-type multi-dose injection device, similar to what is illustrated in FIG. 1. The injection device could be a reusable or disposable device. By disposable device it is meant an injection device that is obtained from the manufacturer preloaded with medicament and cannot be reloaded with new medicament after the initial medicament is exhausted. The device may be a fixed dose or a settable dose and preferably a multi-dose device, however, in some cases it may be beneficial to use a single dose, disposable device.

A typical injection device contains a cartridge or other reservoir of primary medication. This cartridge is typically cylindrical in shape and is usually manufactured in glass. The cartridge is sealed at one end with a rubber bung and at the other end by a rubber septum. The injection device is designed to deliver multiple injections. The delivery mechanism is typically powered by a manual action of the user, however, the injection mechanism may also be powered by other means such as a spring, compressed gas or electrical energy. In a preferred embodiment, the delivery mechanism comprises a spindle that engages a piston in the reservoir. In a further embodiment the spindle is a rotatable piston rod comprising two distinct threads.

In an example, proper filling of a reservoir of a medicated module, such as medicated module 4, may rely on accurate filling of the medicament and the incorporation of an amount of additional 'head-space' in the medicament cavity in order to accommodate manufacturing and assembly tolerances. Such a filling process may result in the presence of air in the pack after filling and closure which—in extreme tolerance conditions, for example—may have the potential to detrimentally reduce the delivered dose volume from the medicated module. One possible solution would be to tighten the tolerances of both the reservoir geometry and the tolerances on the fill accuracy of the filling equipment. This solution route would likely increase manufacturing costs and/or manufacturing complexity, and thus is not ideal for high volume, rapid throughput manufacturing.

In accordance with Applicants' proposed concept, a reservoir assembly is provided that address these concerns. As mentioned above, the reservoir assembly in accordance with Applicants' disclosure beneficially results in little or no air being present in the reservoir cavity after filling. The reservoir assembly in accordance with Applicants' proposed concept generally incorporates two elements: a sump region and the medicament cavity. An example purpose of the sump region is to increase the nominal fill volume relative to the primary cavity volume. This increase may reduce the challenges associated with filling the device due to the possible small volume (e.g., 20-30 microliters (ul)) required by the drug cavity. Other volumes are possible as well, such as higher or lower volumes. In addition, the interface between the sump region and the primary cavity is configured such that during filling air is preferably purged from the drug cavity into the sump region. This air-purging action serves to help minimize any residual air trapped in the medicament cavity and thus minimizes its impact on the dispense volume when the cavity contents are expelled during use. The primary cavity is designed and sized to suit the required volume for the medicated module such that a known and controlled volume of the second medicament will be dispensed when the minimum required dose (e.g., in the range 50 ul) is dispensed from the primary drug delivery device to which the medicated module is attached.

A reservoir assembly in accordance with Applicants' proposed concept generally includes a primary cavity for holding a medicament, a sump region, and a flexible element. The flexible element is configured to allow for fluid communication between the primary cavity and the sump region during a filling process for the reservoir, and the flexible element is also configured to prevent fluid communication between the primary cavity and the sump region after the filling process.

FIG. 11 illustrates a first example of such a reservoir assembly, and FIGS. 13a-f illustrate an example filling process for the reservoir assembly. Further, FIG. 15 illustrates a second example of such a reservoir assembly, and FIGS. 17a-f illustrate an example filling process for the reservoir assembly.

Generally, during a filling process for the reservoir assembly, the medicament from a pressurized filling nozzle will cause a flexible element (e.g., a flexible lower bung) in the reservoir assembly to deflect and thus to create a vent path to the sump region. This vent path will enable air to be purged/forced from the drug cavity and into the sump region. After filling, the pressure may be removed and the flexible element will return to its former position, sealing off the drug cavity from the sump region. The upper bung is then assembled to create the sealed drug cavity. Preferably the stiffness of the flexible element (which may be defined by a combination of material properties and geometry) will be designed such that the hydraulic pressure generated during an in-use dispense action will be insufficient to cause sufficient deflection to re-open this flow path between the drug cavity and the sump region again.

Figure 12B:
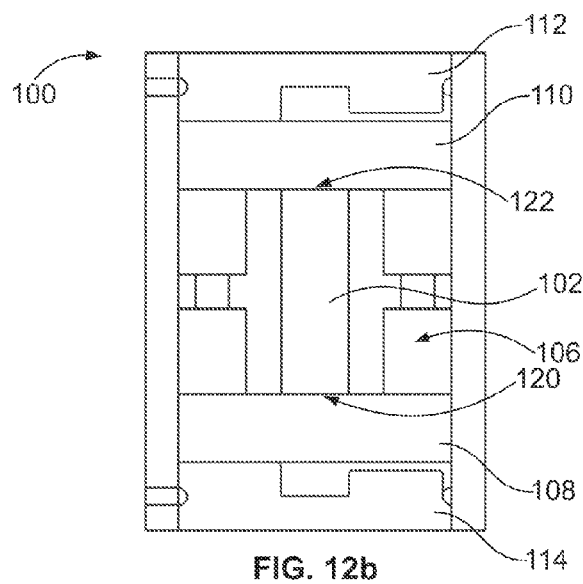
FIG. 12b illustrates a cross-sectional view of the reservoir assembly of FIG. 11.

As mentioned above, a first example of a reservoir assembly in accordance with Applicants' disclosure is illustrated in FIG. 11. In particular, FIG. 11 illustrates a reservoir assembly 100 for a medicated module, such as medicated module 4 (see FIG. 2). FIGS. 12a-b illustrate cross-sectional views of reservoir assembly 100. Reservoir assembly 100 includes a primary cavity 102 for holding a medicament 104 (see FIGS. 13b-f), a sump region 106, and a flexible element 108. The sump region 106 generally acts as a reservoir that may collect excess air and/or medicament 104 from the primary cavity 102 during the filling process of reservoir assembly 100. The primary cavity 102 may be a tubular cavity, and the sump region 106 may be a ring-shaped tubular cavity surrounding the primary cavity. In this example, the flexible element 108 is a distal primary-cavity bung 108. Exemplary materials for the flexible bung include TPE (thermo plastic elastomer) and LSR (liquid silicone rubber). The reservoir assembly 100 also includes a proximal primary-cavity bung 110, a proximal bypass bung 112, and a distal bypass bung 114.

As can be seen in FIG. 12b, the distal primary-cavity bung 108 is located at a distal end 120 of the primary cavity 102, and the proximal primary-cavity bung 110 is located at a proximal end 122 of the primary cavity 102. In addition, the proximal bypass bung 112 is located above the proximal primary-cavity bung 110, whereas the distal bypass bung 114 is located below the distal primary cavity bung 108.

Beneficially, the reservoir assembly 100 may be filled with medicament in a way that minimizes or limits air in the primary cavity 102. The filling and assembly process for reservoir assembly 100 is described with reference to FIGS. 13a-f. These figures depict the reservoir assembly 100 at various stages of the filling and assembly process.

Figures 13A, 13B:
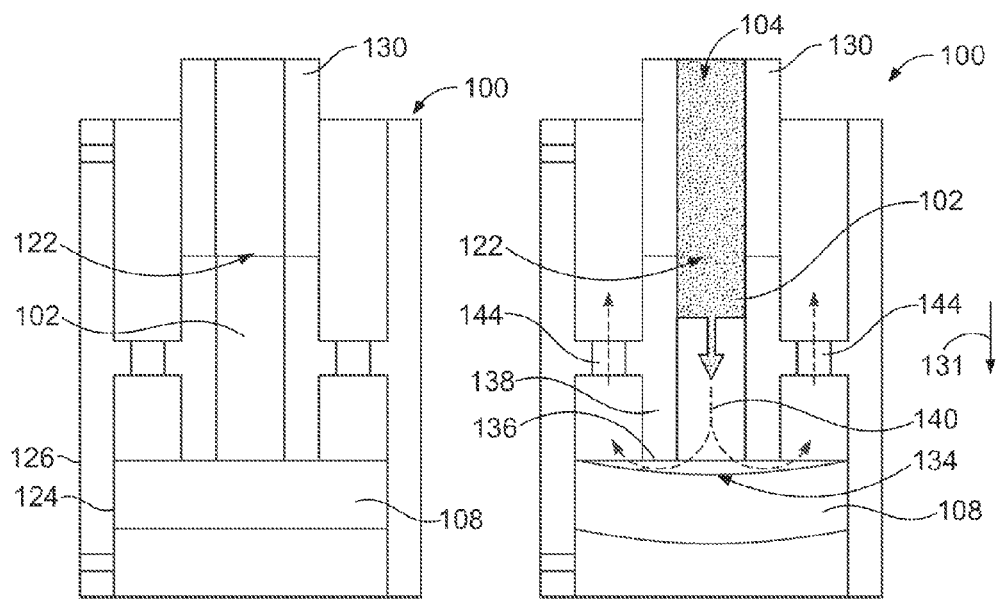
FIGS. 13a-f illustrate the reservoir assembly of FIG. 11 at various stages of the assembly and filling process.

As seen in FIG. 13a, prior to the filling process, the flexible element 108 (i.e., the distal primary-cavity bung 108) may be assembled in the drug reservoir assembly 100. In particular, the distal primary-cavity bung 108 may be placed below the primary cavity 102. Further, the primary-cavity bung 108 may be engaged with the inner wall 124 of the main body 126 of the reservoir assembly 100.

A filling nozzle 130 or similar component of a filling apparatus may be introduced into the reservoir assembly 100. The filling nozzle 130 may form a seal against the proximal surface 122 of the primary cavity 102, as shown in FIG. 13a.

FIG. 13b depicts the filling and assembly process after the filling nozzle 130 begins filling the medicament 104 into the primary cavity 102. The medicament 104 is driven into the primary cavity 102 under pressure. This filling action causes the distal primary-cavity bung 108 to deflect slightly in distal direction 131. For example, in this example, the flexible primary-cavity bung 108 curves slightly under the pressure of the filling action. This deflection of the flexible distal primary-cavity bung creates a vent path 134 for air to escape into the sump region (shown by dashed arrows 140). The vent path 134 is defined by distal end 136 of the primary-cavity outer body 138 and the flexible distal primary-cavity bung 108.

In this example, air in the sump region 106 may escape to the atmosphere via the sump vent channels 144. This allows the system pressure to equalize.

Figures 13C, 13D:
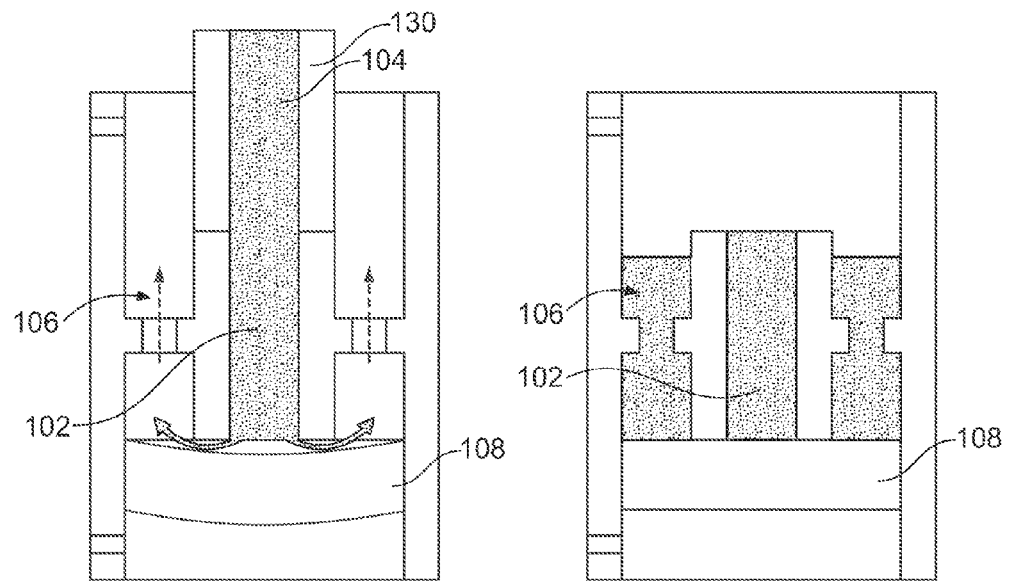

As seen in FIG. 13c, after the primary cavity 102 is filled, the medicament 104 may continue to be dispensed from the filling nozzle 130 until the sump region 106 is partially filled. This beneficially accommodates fill tolerances. In some cases, medicament 104 may enter the sump region 106 before the primary cavity 102 is completely filled.

After the sump region 106 is at least partially filled, the filling nozzle 130 may be retracted, and the flexible primary-cavity bung may return to its previous state (i.e., non-flexed state), as shown in FIG. 13d.

Figures 13E, 13F:
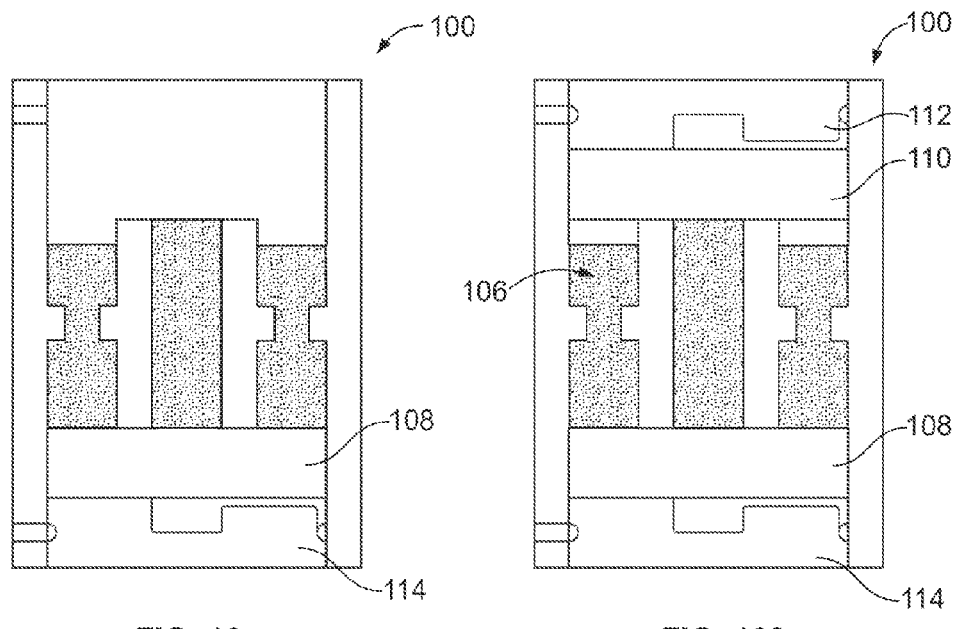

After the primary cavity 102 is filled, the proximal primary-cavity bung 110 and bypass bungs 112, 114 can be added to the reservoir assembly. For example, as shown in FIG. 13e, the distal bypass bung 114 may be assembled to the reservoir assembly 100. The bypass bung 114 may ensure that the flexible primary-cavity bung 108 is securely seated on the end of the primary cavity 102. The proximal primary-cavity bung 110 may then be assembled to the reservoir assembly 100, followed by the proximal bypass bung 112. In an example, the proximal primary-cavity bung 110 may be assembled under a vacuum or a partial vacuum to prevent pre-saturation of the residual air in the reservoir assembly 100. Although FIGS. 13e-f depict the distal bypass bung 114 being added before the proximal primary-cavity bung 110 and proximal bypass bung 112, vice versa may occur. That is, the proximal primary-cavity bung 110 and proximal bypass bung 112 may be added before the distal bypass bung 114.

As mentioned above with respect to FIG. 7, the medicated module may beneficially include a bypass channel configured to allow for priming of the drug delivery device. FIG.

14a illustrates the priming capability of reservoir assembly 100. The bypass side channels 150, 152 allow access to the bypass bungs 112 and 114, respectively. As discussed above, needles 160, 162 may enter the bypass needle wells 154, 156, and a priming dose may travel from the inlet needle 160 to the outlet needle 162 through a bypass channel, as indicated by the path depicted by arrow 158.

Figure 14A:
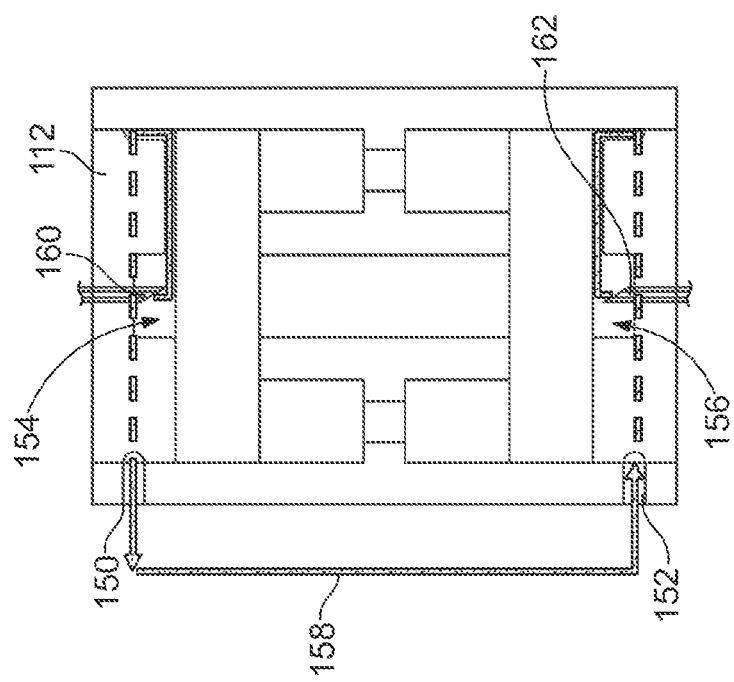
FIGS. 14a-b illustrate the reservoir assembly of FIG. 11 at various operational phases.
Figure 14B:
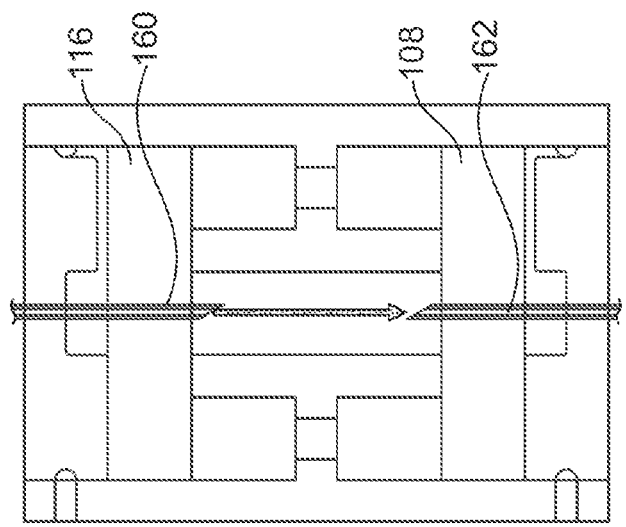

During dispense, the inlet needle 160 pierces the proximal primary-cavity bung 110, and outlet needle 162 pierces the distal primary-cavity bung 108. This results in medicament flow directly from the inlet needle 160 to the outlet needle 162 via the primary cavity 102, as shown in FIG. 14b.

In an example of Applicants' reservoir assembly, the reservoir assembly 100 may include flow-distribution features, such as flow distributor 23 (see FIG. 5), to help ensure "plug flow" in the drug cavity.

A second example of a reservoir assembly in accordance with Applicants' disclosure is illustrated in FIG. 15. This example is similar in many respects to the example of FIG. 11, and thus is not described in as great detail. Many of the possibilities and permutations described above with respect to reservoir assembly 100 are possible in the example of FIG. 15. However, in the example of FIG. 15, the flexible element is a vent valve rather than the distal primary-cavity bung.

In particular, FIG. 15 illustrates a reservoir assembly 200 for a medicated module, such as medicated module 4. FIGS. 16a-b illustrate cross-sectional views of reservoir assembly 200. Reservoir assembly 200 includes a primary cavity 202 for holding a medicament 204 (see FIGS. 17b-f), a sump region 206, and a flexible element 207. The sump region 206 generally acts as a reservoir that may collect excess air and/or medicament 204 from the primary cavity 202 during the filling process of reservoir assembly 200. In this second example, the flexible element 207 is a vent valve 207. The reservoir assembly 200 also includes a proximal primary-cavity bung 210, a proximal bypass bung 212, a distal primary-cavity bung 208, and a distal bypass bung 214.

The vent valve 207 may be a tubular-shaped valve that is disposed around the outer body 238 of the primary cavity 202. As can be seen in FIGS. 15a-b, the distal end of the vent valve 207 is located at the interface between the distal primary-cavity bung 208 and the distal end of the primary cavity 202. In the example shown, the vent valve 207 and the outer body 238 are tightly engaged at the proximal end. Further, in this example, the distal end is engaged to the outer body 238, but is flexible and thus configured to open up to create a flow path during the filling and assembly process.

Similar to the example of FIG. 11, beneficially, the reservoir assembly 200 may be filled with medicament in a way that minimizes or limits air in the primary cavity 202. The filling and assembly process for reservoir assembly 200 is described with reference to FIGS. 17a-f. FIGS. 17a-f depict the reservoir assembly 200 at various stages of the filling and assembly process.

As seen in FIG. 17a, prior to the filling process, the flexible element 207 (i.e., the vent valve 207) and the distal primary-cavity bung may be assembled in the drug reservoir assembly 200. In particular, the distal primary-cavity bung 208 may be placed below the primary cavity 202 and the vent valve 207 may be placed around the outer body 238 of the primary cavity 202. Further, the primary-cavity bung 208 may be engaged with the inner wall 224 of the main body 226 of the reservoir assembly 200.

A filling nozzle 230 or similar component of a filling apparatus may be introduced into the reservoir assembly 200. The filling nozzle 230 may form a seal against the proximal surface 222 of the primary cavity 202, as shown in FIG. 17a.

FIG. 17b depicts the filling and assembly process after the filling nozzle 230 begins filling the medicament 204 into the primary cavity 202. The medicament 204 is driven into the primary cavity 202 under pressure. This filling action causes the vent valve 207 to open, creating a vent path for air to escape into the sump region 206. For example, in this example, the distal end of the vent valve 207 curves slightly under the pressure of the filling action. This curvature of the flexible vent valve 207 creates a vent path 234 for air to escape into the sump region 206. The vent path 234 is defined by the vent valve channels 209, 211, the vent valve 207, and the distal primary-cavity bung 208.

In this example, air in the sump region 206 may escape to the atmosphere 242 via the sump vent channels 244. This allows the system pressure to equalize.

Figure 17C:
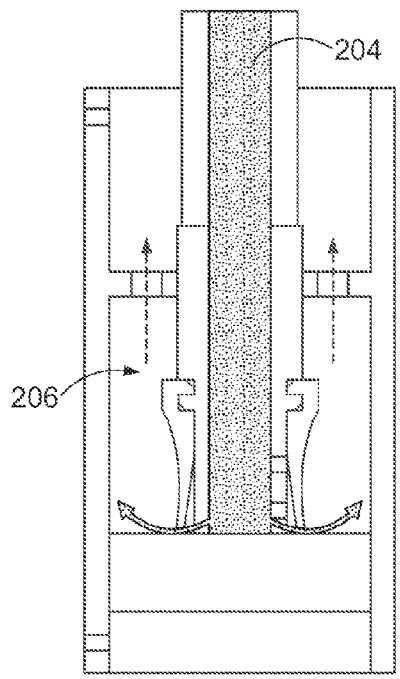
Figure 17D:
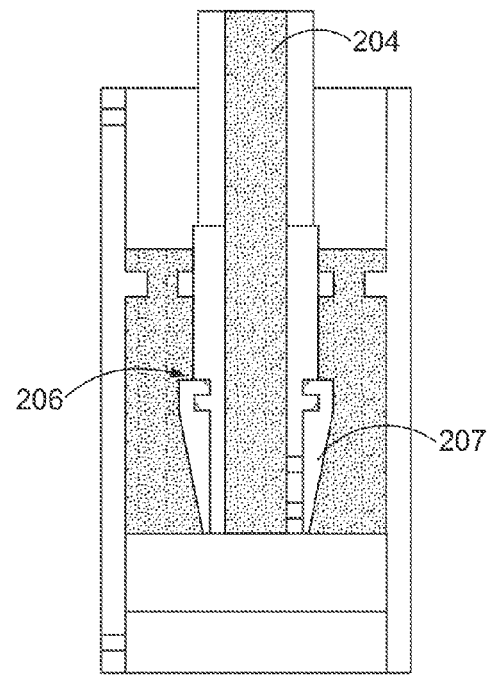

As seen in FIGS. 17c-d, after the primary cavity 202 is filled, the medicament 204 may continue to be dispensed from the filling nozzle 230 until the sump region 206 is partially filled. This beneficially accommodates fill tolerances. In some cases, medicament 204 may enter the sump region 206 before the primary cavity 202 is completely filled.

After the sump region 206 is at least partially filled, the filling nozzle 230 may be retracted, and the flexible vent valve 207 may return to its previous state (i.e., non-flexed state), as shown in FIG. 17d.

Figure 17E:
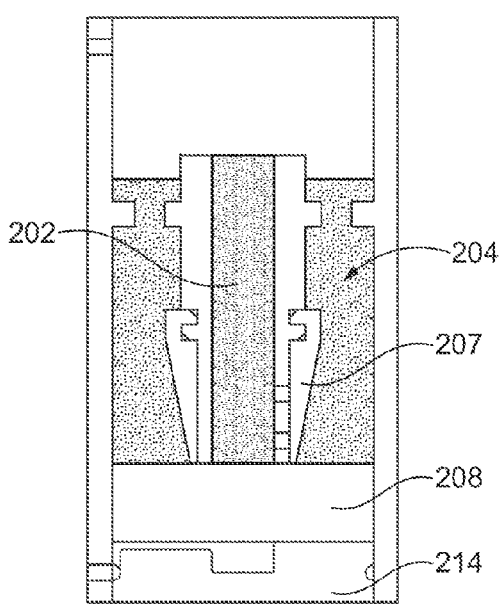
Figure 17F:
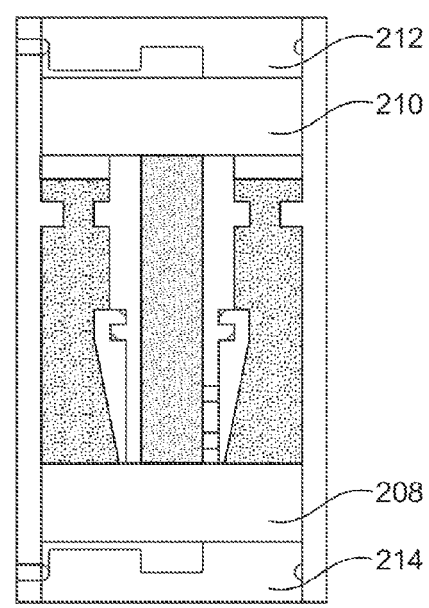

After the primary cavity 202 is filled, the proximal primary-cavity bung 210 and bypass bungs 212, 214 can be added to the reservoir assembly. For example, as shown in FIG. 17e, the distal bypass bung 214 may be assembled to the reservoir assembly 200. The bypass bung 214 may ensure that the flexible primary-cavity bung 208 is securely seated on the end of the primary cavity 202. The proximal primary-cavity bung 210 may then be assembled to the reservoir assembly 200, followed by the proximal bypass bung 212. In an example, the proximal primary-cavity bung 210 may be assembled under a vacuum or a partial vacuum to prevent pre-saturation of the residual air in the reservoir assembly 200. Although FIGS. 17e-f depict the distal bypass bung 214 being added before the proximal primary-cavity bung 210 and proximal bypass bung 212, the vice versa may occur. That is, the proximal primary-cavity bung 210 and proximal bypass bung 212 may be added before the distal bypass bung 214.

Figure 18B:
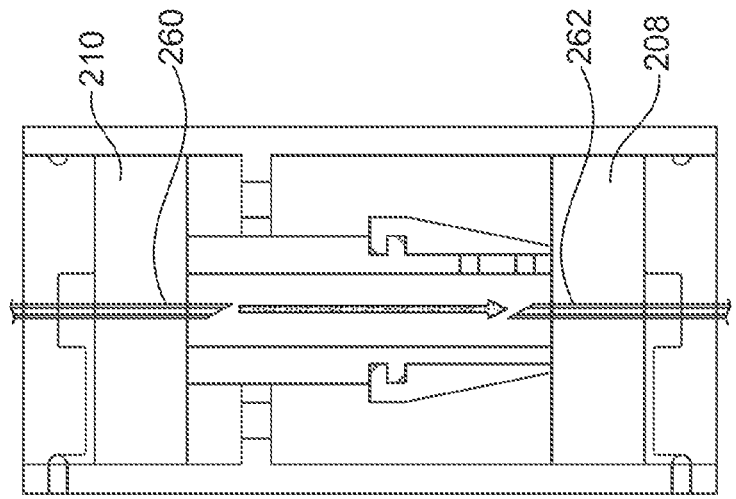
FIGS. 18a-b illustrate the reservoir assembly of FIG. 11 at various operational phases.
Figure 18A:
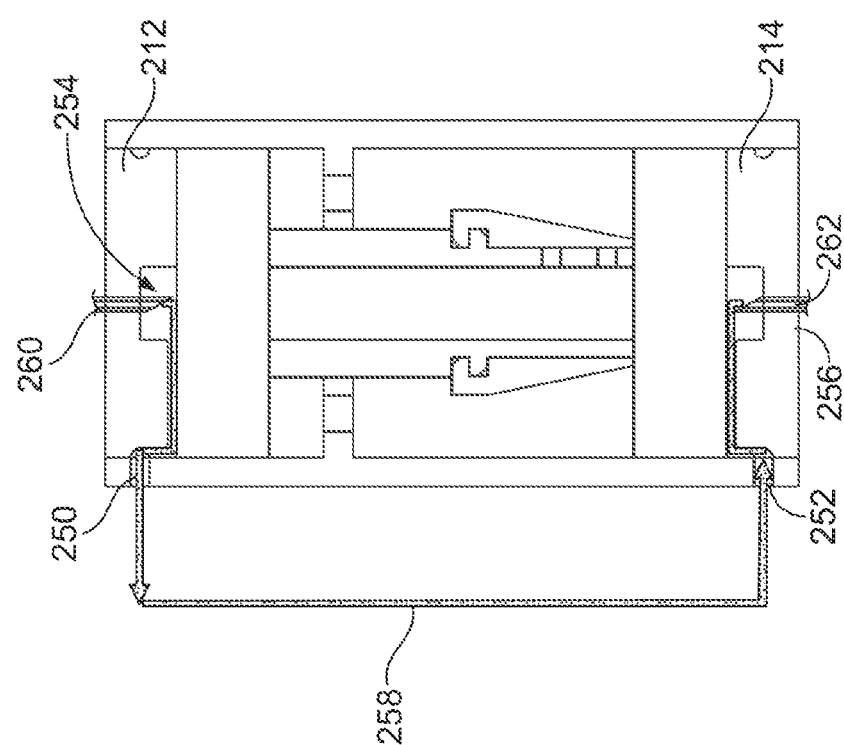

As mentioned above with respect to FIG. 7, a medicated module may beneficially include a bypass channel configured to allow for priming of the drug delivery device. FIG. 18a illustrates the priming capability of reservoir assembly 200. The bypass side channels 250, 252 allow access to the bypass bungs 212 and 214, respectively. As discussed above, needles may enter the bypass needle wells 254, 256, and a priming dose may travel from the inlet needle 260 to the outlet needle 262 through a bypass channel, as indicated by the path depicted by arrow 258.

During dispense, the inlet needle 260 pierces the proximal primary-cavity bung 210, and outlet needle 262 pierces the distal primary-cavity bung 208. This results in medicament flow directly from the inlet needle 260 to the outlet needle 262 via the primary cavity 202, as shown in FIG. 18b.

Similar to the example of FIG. 11, the reservoir assembly 200 may include flow-distribution features, such as flow distributor 23 (see FIG. 5), to help ensure "plug flow" in the drug cavity.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A reservoir assembly for a medicated module, the reservoir assembly comprising:
   a primary cavity for holding a medicament wherein the primary cavity has a proximal end, a distal end, and is located along a central axis of the medicated module; a sump region, wherein the sump region comprises one or more cavities arranged around the primary cavity;
   a flexible element, wherein the flexible element is configured to allow for fluid communication between the primary cavity and the sump region during a pressure filling process for the reservoir assembly, and wherein the flexible element is configured to prevent fluid communication between the primary cavity and the sump region after the filling process, when the pressure is removed;
   a proximal primary-cavity bung configured to seal the proximal end of the primary cavity; and
   a distal primary-cavity bung configured to seal the distal end of the primary cavity.

2. The reservoir assembly of claim 1, wherein the flexible element at least partially defines a vent path between the primary cavity and the sump region when the flexible element is deflected.

3. The reservoir assembly of claim 2, wherein the vent path allows air to flow from the primary cavity to the sump region during the filling process.

4. The reservoir assembly of claim 1, wherein the flexible element comprises a flexible primary-cavity bung.

5. The reservoir assembly of claim 1, wherein the flexible element comprises a vent valve.

6. The reservoir assembly of claim 5, further comprising at least one vent-valve channel between the primary cavity and the vent valve.

7. The reservoir assembly of claim 1, wherein the sump region comprises a sump-region vent channel.

8. The reservoir assembly of claim 1, wherein the medicament fills the primary cavity and wherein the medicament at least partially fills the sump region.

9. The reservoir assembly of claim 1, wherein the primary cavity comprises a tubular cavity, and wherein the sump region comprises a ring-shaped tubular cavity surrounding the primary cavity.

10. The reservoir assembly of claim 1, wherein the sump region is configured to collect excess air and/or medicament from the primary cavity during a filling process of the reservoir assembly.

11. A reservoir assembly for a medicated module, the reservoir comprising:
    a primary cavity for holding a medicament wherein the primary cavity is located along a central axis of the medicated module; a sump region, wherein the sump region comprises one or more cavities arranged around the primary cavity;
    a flexible element, wherein the flexible element is configured to allow for fluid communication between the primary cavity and the sump region during a pressure filling process for the reservoir assembly, and wherein the flexible element is configured to prevent fluid communication between the primary cavity and the sump region after the filling process, when the pressure is removed;
    a proximal bypass bung;
    a distal bypass bung; and
    a bypass channel, wherein the proximal bypass bung and the distal bypass bung are each in communication with the bypass channel, wherein the bypass channel is configured to allow for a priming step.

* * * * *